United States Patent
Ishibashi et al.

(10) Patent No.: US 12,016,757 B2
(45) Date of Patent: Jun. 25, 2024

(54) ABSORBENT ARTICLE

(71) Applicant: Kao Corporation, Tokyo (JP)

(72) Inventors: Kyoko Ishibashi, Utsunomiya (JP);
Yuko Fukuda, Tochigi (JP); Yasuyuki Okuda, Utsunomiya (JP); Jun Kajiwara, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 1274 days.

(21) Appl. No.: 16/609,718

(22) PCT Filed: Jun. 21, 2017

(86) PCT No.: PCT/JP2017/022923
§ 371 (c)(1),
(2) Date: Oct. 30, 2019

(87) PCT Pub. No.: WO2018/235211
PCT Pub. Date: Dec. 27, 2018

(65) Prior Publication Data
US 2021/0100695 A1    Apr. 8, 2021

(51) Int. Cl.
*A61F 13/49* (2006.01)
*A61F 13/514* (2006.01)

(52) U.S. Cl.
CPC .. *A61F 13/49009* (2013.01); *A61F 13/51464* (2013.01); *A61F 2013/49023* (2013.01)

(58) Field of Classification Search
CPC .......... A61F 13/49009; A61F 13/51464; A61F 2013/49023; A61F 13/49015; A61F 13/49012; A61F 13/49; A61F 13/514
See application file for complete search history.

(56) References Cited

U.S. PATENT DOCUMENTS

2001/0029141 A1    10/2001  Mizutani et al.
2005/0131366 A1*    6/2005  Shimada ........... A61F 13/51496
                                                   428/137
(Continued)

FOREIGN PATENT DOCUMENTS

CN    1678271 A    10/2005
CN    1947674 A    4/2007
(Continued)

OTHER PUBLICATIONS

International Search Report for PCT/JP2017/022923 (PCT/ISA/210) mailed on Aug. 29, 2017.

*Primary Examiner* — Jessica Arble
(74) *Attorney, Agent, or Firm* — Birch, Stewart, Kolasch & Birch, LLP

(57) ABSTRACT

An absorbent article (1) of the present invention has, in at least one of a front portion and a rear portion thereof, an elasticized portion (G) that is stretchable and contractible in an article lateral direction (Y). The elasticized portion (G) has an outer sheet (22) to be disposed on a side that is away from the skin of a wearer, an inner sheet (23) to be disposed on a side that is closer to the skin of the wearer than the outer sheet (22) is, and a plurality of elastic members (24) that are arranged between the outer and inner sheets in a state in which the elastic members are stretched in the article lateral direction (Y). The outer sheet (22) and the inner sheet (23) are partially joined to each other at a joined region (26). The joined region (26) is sandwiched between non-joined regions (36) where the outer sheet (22) and the inner sheet (23) are not continuously joined to each other in an article longitudinal direction or the article lateral direction. A plurality of the joined regions (26) and a plurality of the non-joined regions (36) are repeatedly arranged in the article longitudinal direction or the article lateral direction. The outer sheet (22) is configured to be deformable so as to bulge (Continued)

toward a non-skin-facing surface side due to contraction of the elastic members (24) and form a plurality of folds (29) along the article longitudinal direction (X) or the article lateral direction (Y). The absorbent article (1) has holes penetrating the outer sheet (22) at positions in the folds (29) formed by the outer sheet (22), the positions overlapping the elastic members (24) in a thickness direction.

20 Claims, 8 Drawing Sheets

(56) References Cited

U.S. PATENT DOCUMENTS

| | | | |
|---|---|---|---|
| 2005/0267431 A1 | 12/2005 | Sasaki et al. | |
| 2009/0082746 A1* | 3/2009 | Thomas | A61F 13/512 |
| | | | 604/378 |
| 2011/0319853 A1* | 12/2011 | Yamashita | A61F 13/496 |
| | | | 604/385.3 |
| 2012/0191057 A1* | 7/2012 | Takino | A61F 13/49413 |
| | | | 604/385.29 |
| 2016/0184145 A1 | 6/2016 | Morimoto | |
| 2018/0008481 A1 | 1/2018 | Takahashi et al. | |
| 2018/0014979 A1 | 1/2018 | Fujita | |
| 2018/0014984 A1 | 1/2018 | Sakai | |
| 2018/0015709 A1 | 1/2018 | Takeuchi | |
| 2018/0028371 A1 | 2/2018 | Takaishi | |
| 2018/0147094 A1 | 5/2018 | Takeuchi | |

FOREIGN PATENT DOCUMENTS

| | | |
|---|---|---|
| CN | 101541284 A | 9/2009 |
| CN | 102405034 A | 4/2012 |
| EP | 3 485 859 A1 | 5/2019 |
| JP | 2001-328191 A | 11/2001 |
| JP | 2009-83487 A | 4/2009 |
| JP | 2010-133071 A | 6/2010 |
| JP | 3166677 U | 3/2011 |
| JP | 2011-78477 A | 4/2011 |
| JP | 2014-4115 A | 1/2014 |
| JP | 2014-188189 A | 10/2014 |
| JP | 2015-92957 A | 5/2015 |
| JP | 2015-107223 A | 6/2015 |
| JP | 2015-128573 A | 7/2015 |
| JP | 2015-192862 A | 11/2015 |
| JP | 6001810 B1 | 10/2016 |
| JP | 2017-64225 A | 4/2017 |
| WO | WO 2016/208280 A1 | 12/2016 |
| WO | WO 2017/175288 A1 | 10/2017 |
| WO | WO 2018/042553 A1 | 3/2018 |

* cited by examiner

ABSORBENT ARTICLE

TECHNICAL FIELD

The present invention relates to an absorbent article.

BACKGROUND ART

Generally, an absorbent article such as a diaper includes an outer cover that forms a surface of the absorbent article on a side that does not face the skin of a wearer and an absorbent assembly that is fixed to a skin-facing surface side of the outer cover. From the standpoint of ensuring high flexibility and a favorable tactile feel, an absorbent article is known in which a plurality of gathers along a longitudinal direction of the absorbent article are formed in the outer cover. Moreover, from the standpoint of ensuring breathability, an absorbent article is known in which a plurality of holes are formed in a sheet constituting the outer cover.

For example, the applicant of the present invention has previously proposed a pull-on absorbent article including an outer cover having a first sheet and a second sheet that are joined to each other at a plurality of joined regions as well as elastic members that are arranged between these sheets, as well as an absorbent assembly (see Patent Literature 1). Tubular portions are formed in the outer cover, the tubular portions constituting gathers as a result of the first sheet and the second sheet deforming due to the contraction of the elastic members. Moreover, a plurality of holes that are in communication with the inside of the tubular portions are intermittently formed in the first sheet. According to the technology of Patent Literature 1, the outer cover is soft and has an excellent tactile feel because the plurality of tubular portions give volume in the thickness direction, and the outer cover also has high breathability because the holes are provided in the first sheet constituting the outer cover.

Moreover, the applicant of the present invention has previously proposed an absorbent article in which hollow gathers are formed in an outer cover, and joined regions at which an outer sheet and an inner sheet that constitute the outer cover are joined to each other as well as holes penetrating the outer sheet and the inner sheet are formed in an overlapping manner (see Patent Literature 2). According to the technology of Patent Literature 2, moisture within the absorbent article is easily allowed to escape to the outside because hollow portions between the gathers serve as ventilation paths, and the outer cover has excellent flexibility because the joined regions and the holes are formed in an overlapping manner.

Moreover, the applicant of the present invention has previously proposed an absorbent article including an outer cover having an outer sheet member and an inner sheet member as well as elastic members that are arranged between these sheet members, wherein each of the outer sheet member and the inner sheet member has holes, and the holes of the outer sheet and the holes of the inner sheet are formed at positions that do not overlap each other (see Patent Literature 3). According to the technology of Patent Literature 3, since each of the layer sheet member and the inner sheet member has the holes, the breathability is improved, and trapping of heat and moisture within the absorbent article when worn is reduced.

CITATION LIST

Patent Literature

Patent Literature 1: JP 2011-78477A
Patent Literature 2: JP 2015-192862A
Patent Literature 3: JP 2015-128573A

SUMMARY OF INVENTION

The present invention relates to an absorbent article having a front portion to be disposed on a front side of a wearer, a rear portion to be disposed on a rear side of the wearer, and a crotch portion located between the front portion and the rear portion. The absorbent article has an elasticized portion that is stretchable and contractible in an article lateral direction in at least one of the front portion and the rear portion. The elasticized portion has an outer sheet to be disposed on a side that is away from the skin of the wearer, an inner sheet to be disposed on a side that is closer to the skin of the wearer than the outer sheet is, and a plurality of elastic members that are arranged between the outer and inner sheets in a state in which the elastic members are stretched in the article lateral direction. The outer sheet and the inner sheet are partially joined to each other at a joined region. The joined region is sandwiched between non-joined regions where the outer sheet and the inner sheet are not continuously joined to each other in an article longitudinal direction or the article lateral direction. A plurality of the joined regions and a plurality of the non-joined regions are repeatedly arranged in the article longitudinal direction or the article lateral direction. The outer sheet is configured to be deformable so as to bulge toward a non-skin-facing surface side due to contraction of the elastic members and form a plurality of folds along the article longitudinal direction. The absorbent article has holes penetrating the outer sheet at positions in the folds formed by the outer sheet, the positions overlapping the elastic members in a thickness direction.

DESCRIPTION OF EMBODIMENTS

It was found that if gathers are formed by making elastic members contract in order to improve the flexibility and the breathability of an outer cover, the breathability of a section that is pressed by the elastic members that have contracted is likely to be low. To address this issue, it was attempted to suppress the decrease in breathability due to pressing by the elastic members by providing holes in a skin-facing surface-side sheet of the outer cover, but the breathability did not significantly improve.

Therefore, the present invention relates to providing an absorbent article that has excellent breathability.

Hereinafter, an absorbent article of the present invention will be described based on preferred embodiments thereof with reference to the drawings.

Figure 1:
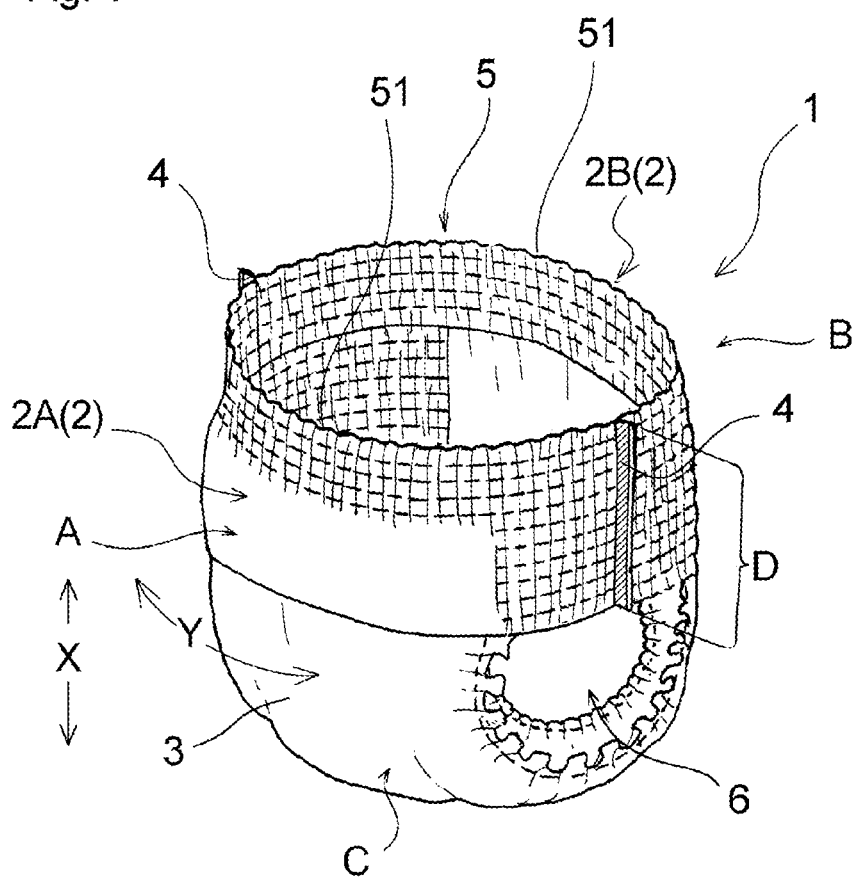
FIG. 1 is a perspective view showing a state in which a pull-on disposable diaper, which is an embodiment of the present invention, is used (worn).

A disposable diaper 1, which is an embodiment of the present invention, will be described with reference to FIGS. 1 to 3. As shown in FIG. 1, the disposable diaper 1 of the present embodiment is a pull-on disposable diaper and includes an outer cover 2 and an absorbent assembly 3 fixed to the outer cover 2. Also, the diaper 1 has a front portion A and a rear portion B to be disposed on a front side and a rear side, respectively, of a wearer when the wearer wears the diaper 1. Both end portions of the front portion A in an article lateral direction Y are respectively joined to both end portions of the rear portion B in the article lateral direction Y to form a pair of side seals 4,4. Moreover, as a result of these joining, a waist opening 5 and a pair of leg openings 6 are formed. Between the front portion A and the rear portion B, the diaper 1 has a crotch portion C to be disposed between the wearer's legs.

The outer cover 2 of the diaper 1 of the present embodiment has a front panel 2A that forms the front portion A and a rear panel 2B that forms the rear portion B. The front panel 2A and the rear panel 2B are joined to each other at the pair of side seals 4,4. As shown in FIG. 2, the absorbent assembly 3 is fixed bridging a central portion of the front panel 2A in the article lateral direction Y and a central portion of the rear panel 2B in the article lateral direction Y. Portions of the absorbent assembly 3 that overlap the front panel 2A and the rear panel 2B, respectively, are entirely or partially joined to the two panels 2A and 2B using a known joining means such as an adhesive.

The outer cover 2 may have a narrow region, for example, a region having a width of not more than 10 mm, in which the front panel 2A and the rear panel 2B are not joined to each other, at both ends of the front or rear panel in the article lateral direction Y. This case is also included in the case where the front portion A and the rear portion B are joined to each other at both of their end portions in the article lateral direction Y.

Figure 2:
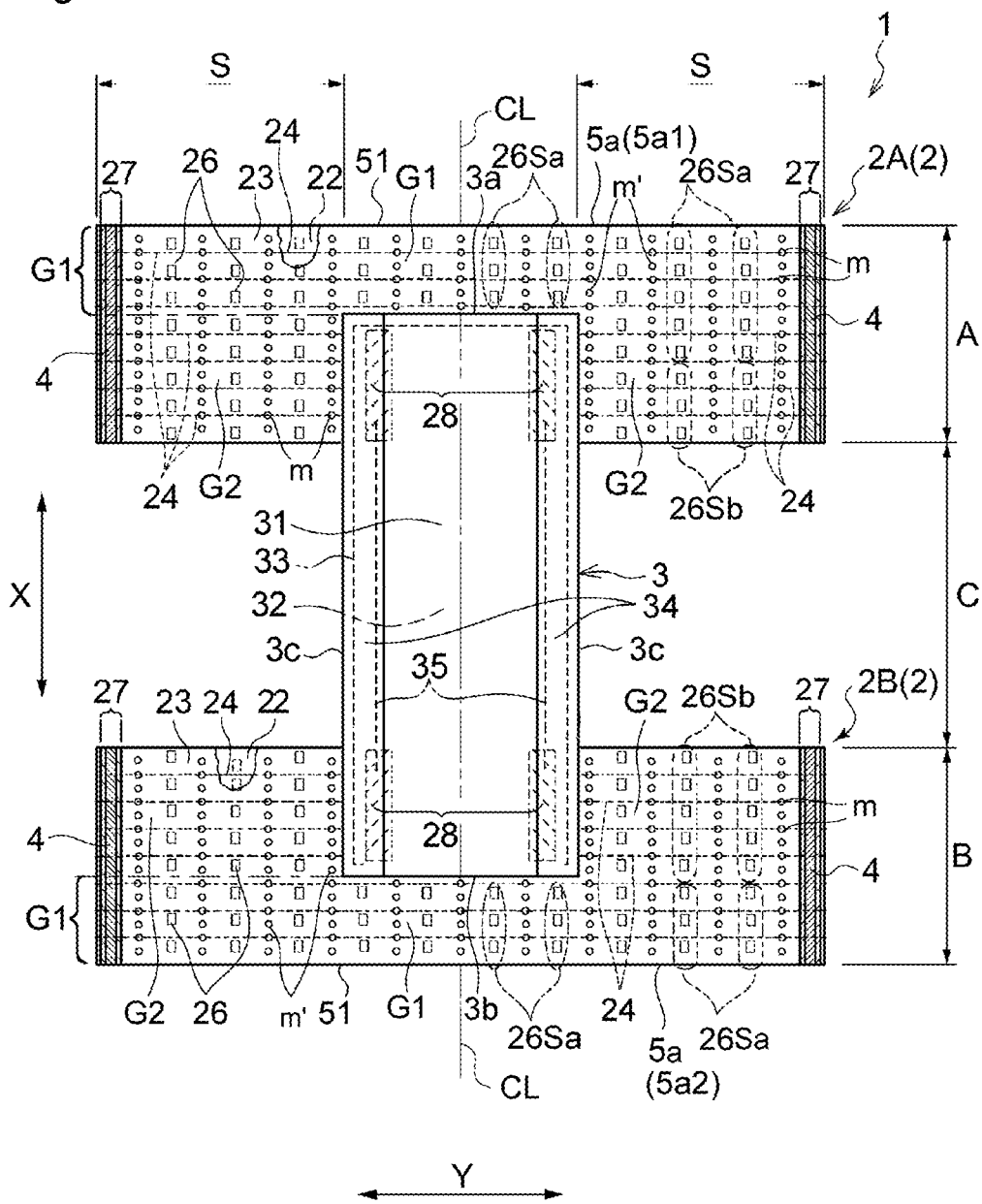
FIG. 2 is a flat-out plan view of the diaper shown in FIG. 1 in its flat-out, uncontracted state when viewed from a skin-facing surface side.

As shown in FIG. 2, the diaper 1 of the present embodiment is formed to be symmetrical with respect to an article longitudinal direction center line CL that extends in an article longitudinal direction X. Accordingly, for the symmetrical portions, the following description mainly gives a description of the right side in FIG. 2; however, the left side has a similar configuration to the right side except that the left side is the mirror image of the right side.

It should be noted that the article longitudinal direction X corresponds to the front-rear direction of the wearer. More specifically, the article longitudinal direction X is the direction from a portion to be disposed on the front side of the wearer to a portion to be disposed on the rear side of the wearer via a portion to be disposed between the wearer's legs, and is usually the same as a longitudinal direction of the absorbent assembly 3. On the other hand, as shown in FIG. 2, the article lateral direction Y is the direction that is perpendicular to the article longitudinal direction X in a state in which an absorbent article such as a diaper is flat-out and uncontracted, and as shown in FIG. 1, the article lateral direction Y is the same as a circumferential direction of a tubular below-waist portion D that is formed by the front portion A and the rear portion B being connected to each other. Moreover, in the front portion A and the rear portion B, the article longitudinal direction X corresponds to an upper-lower direction when the absorbent article is worn, and thus, in each of the front portion A and the rear portion B, the waist opening 5 side is also referred to as an upper side or an upward side, and the crotch portion C side as a lower side or a downward side.

In this specification, "skin-facing surface" refers to either one of the front and rear surfaces of each member constituting the absorbent assembly 3, such as a topsheet 31, which will be described later, that is to be disposed closer to the skin of the wearer when the absorbent article is worn, and "non-skin-facing surface" refers to either one of the front and rear surfaces of each member constituting the absorbent assembly 3, such as the topsheet 31, which will be described later, that is to be disposed facing the side opposite to the skin of the wearer when the absorbent article is worn.

In the diaper 1 of the present embodiment, as shown in FIG. 2, the front panel 2A and the rear panel 2B constituting the outer cover 2 each include an outer sheet 22 constituting an outer surface of the diaper, an inner sheet 23 disposed on an inner surface side of the outer sheet 22, and a plurality of filamentous elastic members 24 that are arranged between the two sheets 22 and 23 in a stretched state. Each of the front panel 2A and the rear panel 2B has a waist elasticized portion G1 and below-waist lower elasticized portions G2. In the following description, the waist elasticized portion G1 and the below-waist lower elasticized portions G2 will also be collectively referred to as an "elasticized portion G". In the diaper 1 of the present embodiment, the outer sheet 22, which constitutes the outer surface of the diaper, is an outer sheet to be disposed on a side that is away from the skin of the wearer, and the inner sheet 23 is an inner sheet to be disposed on a side of the outer cover 2 that is closer to the skin of the wearer than the outer sheet is. This inner sheet 23 is an "inner sheet to be disposed on a side that is closer to the skin of the wearer than the outer sheet is" of the present invention.

The waist elasticized portions G1 are formed outward of respective longitudinal ends 3a and 3b of the absorbent assembly 3 in the article longitudinal direction X of the diaper 1. The waist elasticized portions G1 are formed in a circumferential edge portion of the waist opening 5, and are to be disposed on a waist portion of the wearer when the diaper is worn. In each of the front panel 2A and the rear panel 2B, the below-waist lower elasticized portions G2 are formed below the waist elasticized portion G1 and above lower ends of the side seals 4.

In the waist elasticized portions G1 and the below-waist lower elasticized portions G2 of the present embodiment, the outer sheet 22 and the inner sheet 23 are joined to each other at joined region rows 26S in each of which a plurality of intermittent joined regions 26a are intermittently formed and lined up in a straight line in the article longitudinal direction X. The joined region rows 26S extending in the article longitudinal direction X are arranged such that a plurality of joined region rows 26S are formed at intervals in the article lateral direction Y. In this manner, the diaper 1 has joined regions at which the outer sheet 22 and the inner sheet 23 are partially joined to each other.

More specifically, as shown in FIG. 2, in the waist elasticized portion G1 of each of the front panel 2A and the rear panel 2B, as joined regions 26 at which the outer sheet 22 and the inner sheet 23 are fusion-bonded to each other, a plurality of intermittent joined regions 26a are intermittently formed so as to be lined up in the article longitudinal direction X, and a plurality of joined region rows 26Sa each constituted by a plurality of the intermittent joined regions 26a are formed at intervals in the article lateral direction Y. Joined regions 26 that are formed intermittently or continuously extending in the article longitudinal direction X like the joined region rows 26Sa constituted by the plurality of intermittent joined regions 26a are also referred to as the longitudinal joined regions 26.

Each of the longitudinal joined regions 26 of the present embodiment is sandwiched between corresponding non-joined regions 36 where the outer sheet 22 and the inner sheet 23 are not continuously joined to each other in the article longitudinal direction X. More specifically, the longitudinal joined regions 26 and the non-joined regions 36, which extend in the longitudinal direction X, are alternatingly arranged side-by-side in the article lateral direction Y. Furthermore, a plurality of intermittent joined regions 26a constituting each joined region row 26Sa are sandwiched between corresponding non-joined regions 36 where the outer sheet 22 and the inner sheet 23 are not continuously joined to each other in the article lateral direction Y.

Moreover, in the below-waist lower elasticized portions G2 of each of the front panel 2A and the rear panel 2B as well, intermittent joined regions 26a at which the outer sheet 22 and the inner sheet 23 are fusion-bonded to each other are intermittently formed in such a manner as to be lined up in the article longitudinal direction X. Also, a plurality of joined region rows 26Sb each constituted by a plurality of intermittent joined portions 26a lined up in the article longitudinal direction X are formed at intervals in the article lateral direction Y.

Although the diaper 1 of the present embodiment has, as the longitudinal joined regions 26, the joined region rows 26S that are each formed intermittently extending in the article longitudinal direction X, the longitudinal joined regions 26 may also be formed continuously extending in the article longitudinal direction X. The plurality of longitudinal joined regions 26 are formed at intervals in the article lateral direction.

As described above, the diaper 1 of the present embodiment has, as joined regions at which the outer sheet 22 and the inner sheet 23 are partially joined to each other, the longitudinal joined regions 26 intermittently or continuously extending in the article longitudinal direction; however, the joined regions may also be lateral joined regions intermittently or continuously extending in the article lateral direction. In the case where the joined regions are lateral joined regions, the lateral joined regions are arranged at intervals or continuously in the article longitudinal direction X and are each sandwiched between non-joined regions where the outer sheet 22 and the inner sheet 23 are not continuously joined to each other in the article longitudinal direction X. In addition, a plurality of lateral joined regions and a plurality of non-joined regions are repeatedly arranged in the article longitudinal direction. Moreover, each of the non-joined regions 36, where the outer sheet 22 and the inner sheet 23 are not joined to each other, may continuously extend in either one or both of the article longitudinal direction X and the article lateral direction Y. Also, in the joined regions at which the outer sheet 22 and the inner sheet 23 are joined to each other, although the outer sheet and the inner sheet may be directly joined to each other as in the present embodiment, the outer sheet and the inner sheet may also be joined to each other via another member (e.g., an elastic member or the like).

In side regions S,S of each of the front panel 2A and the rear panel 2B, each joined region row 26Sa of the waist elasticized portion G1 and the corresponding joined region row 26Sb of the below-waist lower elasticized portions G2 together form a single continuous row in the article longitudinal direction X. The side regions S,S are regions that are located outward of both lateral side edges 3c,3c, respectively, of the absorbent assembly 3 in the article lateral direction Y.

In the following description, the joined region rows 26Sa in the waist elasticized portions G1 and the joined region rows 26Sb in the below-waist lower elasticized portions G2 will also be collectively referred to as the joined region rows 26S.

In the waist elasticized portions G1 of the diaper 1 of the present embodiment, with respect to all of the joined region rows 26Sa, the positions of the longitudinal joined regions 26 in the article longitudinal direction X are substantially the same. Moreover, a plurality of elastic members 24 are arranged so as to individually extend in the article lateral direction Y while passing through gaps between the joined regions in each of the plurality of joined region rows 26Sa. That is to say, in the waist elasticized portions G1, the elastic members 24 are arranged passing between the longitudinal joined regions 26, which constitute the joined region rows 26Sa, without being fixed to the longitudinal joined regions 26. All of the plurality of elastic members 24 are arranged between the outer sheet 22 and the inner sheet 23.

Similarly, in the below-waist lower elasticized portions G2,G2 as well, with respect to all of the joined region rows 26Sb, the positions of the longitudinal joined regions 26 in the article longitudinal direction X are substantially the same. Moreover, a plurality of elastic members 24 are arranged so as to individually extend in the article lateral direction Y while passing through gaps between the joined regions in each of the plurality of joined region rows 26Sb. That is to say, in the below-waist lower elasticized portions G2, the elastic members 24 are arranged passing between the longitudinal joined regions 26, which constitute the joined region rows 26Sb, without being fixed to the longitudinal joined regions 26. All of the plurality of elastic members 24 are arranged between the outer sheet 22 and the inner sheet 23 as well.

As described above, in the waist elasticized portions G1 and the below-waist lower elasticized portions G2 of the present embodiment, the longitudinal joined regions 26 and the elastic members 24 do not overlap. Moreover, all of the plurality of elastic members 24 of the present embodiment are arranged between the outer sheet 22 and the inner sheet 23.

As shown in FIG. 2, in the diaper 1 of the present embodiment, both of the front panel 2A and the rear panel 2B have a pair of outer lateral side fixing regions 27 where the outer sheet 22 and the inner sheet 23 are joined to each other via an adhesive, the pair of outer lateral side fixing regions 27 being respectively located on opposite sides of the article longitudinal direction center line CL. Moreover, the front panel 2A and the rear panel 2B both have assembly-side fixing regions 28 where the outer sheet 22 and the inner sheet 23 are joined to each other via an adhesive, the assembly-side fixing regions 28 being located in the vicinity of the respective lateral side edges 3c of the absorbent assembly 3. In each of the front panel 2A (front portion A) and the rear panel 2B (rear portion B), the pair of outer lateral side fixing regions 27 are formed at locations that are spaced apart outward (toward the side seals) from the respective assembly-side fixing regions 28 in the article lateral direction Y. More specifically, the pair of outer lateral side fixing regions 27 are formed at or in the vicinity of respective end portions of each of the front panel 2A and the rear panel 2B in the article lateral direction Y. It is preferable that the outer lateral side fixing regions 27 entirely or partially overlap the corresponding side seals 4.

In each of the waist elasticized portions G1, the plurality of elastic members 24 are arranged extending between the pair of outer lateral side fixing regions 27, and these elastic members 24 are fixed between the sheets 22 and 23 in each of the pair of outer lateral side fixing regions 27, but are not fixed to any of the sheets 22 and 23 between the outer lateral side fixing regions 27.

On the other hand, in each of the below-waist lower elasticized portions G2, the plurality of elastic members 24 are arranged extending between an outer lateral side fixing region 27 and an assembly-side fixing region 28, and these elastic members 24 are fixed between the sheets 22 and 23 in each of the outer lateral side fixing region 27 and the assembly-side fixing region 28, but are not fixed to any of the sheets 22 and 23 between the outer lateral side fixing region 27 and the assembly-side fixing region 28.

As shown in FIG. 2, the assembly-side fixing regions 28 may be formed so as to entirely overlap the absorbent assembly 3. However, the assembly-side fixing regions 28 may also be formed so as to extend from the inside to the outside of the corresponding lateral side edges 3c of the absorbent assembly 3. Moreover, the assembly-side fixing regions 28 may also be formed outside the corresponding lateral side edges 3c of the absorbent assembly 3 in the diaper lateral direction. It should be noted that the embodiment in which the assembly-side fixing regions 28 entirely overlap the absorbent assembly 3 includes both of an embodiment in which the position of an outer end portion of each of the assembly-side fixing regions 28 in the diaper lateral direction coincides with the position of the corresponding lateral side edge 3c of the absorbent assembly 3 and an embodiment in which each of the assembly-side fixing regions 28 is formed at a predetermined distance from the corresponding lateral side edge 3c of the absorbent assembly 3.

Moreover, in the waist elasticized portions G1, the plurality of joined region rows 26Sa are formed at substantially regular intervals in the article lateral direction Y. More specifically, multiple joined region rows 26Sa are arranged at substantially regular intervals between the vicinity of one of the outer lateral side fixing regions 27 and the vicinity of the other outer lateral side fixing region 27. In the below-waist lower elasticized portions G2 as well, the plurality of joined region rows 26Sb are formed at substantially regular intervals between the vicinity of one of the outer lateral side fixing regions 27 and the vicinity of the other outer lateral side fixing region 27. However, between the pair of assembly-side fixing regions 28, no elastic members 24 are arranged, or the elastic members 24 are arranged in a state in which the elastic members 24 are subjected to processing, such as cutting, for preventing elasticity from developing.

Since the elastic members 24 are arranged in the elasticized portion G in a state in which the elastic members 24 are stretched in the article lateral direction Y, the elasticized portion G is stretchable and contractible in the article lateral direction Y. In the waist elasticized portions G1 and the below-waist lower elasticized portions G2 of the present embodiment, as shown in FIGS. 3 and 6, respectively, due to the contraction of the elastic members 24, which are arranged between the outer sheet 22 and the inner sheet 23 in the stretched state, portions of the outer sheet 22 that are located between the longitudinal joined regions 26 adjacent to one another in the article lateral direction Y deforms so as to bulge in the thickness direction of the outer sheet 22, thereby forming a plurality of folds 29 along the article longitudinal direction X and also forming hollow portions 30 between the two sheets 22 and 23. As shown in FIG. 3, the contraction of the elastic members 24 causes the outer sheet 22 to deform so as to bulge toward the non-skin-facing surface side, and thereby forming a plurality of folds along the article longitudinal direction X. The folds 29 are formed between the longitudinal joined regions 26 adjacent to one another in the article lateral direction Y, that is, in the non-joined regions 36, which each continuously extend in the article longitudinal direction X.

It should be noted that although the outer cover 2 shown in FIGS. 3 and 6 has the folds 29 formed in the outer sheet 22, the folds 29 may also be formed in both of the sheets 22 and 23, that is, the outer sheet 22 and the inner sheet 23. The inner sheet 23 of the present embodiment deforms so as to bulge toward the skin-facing surface side as shown in FIG. 3, thereby forming a plurality of folds along the article longitudinal direction X.

When the diaper 1 of the present embodiment is worn, the elastic members 24 press the inner sheet 23 against the skin side, and thus, a space is formed between the inner sheet 23 and the outer sheet 22 in each of the non-joined regions. In particular, in portions where the elastic members 24 are present, the inner sheet 23 is sandwiched between the skin and the elastic members 24 and comes into close contact with the body in a state in which the folds 29 are flattened. Portions of the outer sheet 22 that correspond to those portions deform so as to bulge toward the non-skin side. In the diaper 1, since the joined regions 26 are sandwiched between the non-joined regions, where the outer and inner sheets are not continuously joined to each other in the article longitudinal direction X, the folds 29 along the article longitudinal direction X are formed, and the hollow portions 30 are formed inside the folds 29.

It is preferable that the above-described folds 29 are formed in the elasticized portion G at least in its natural state, and it is preferable that even in a state in which the article is worn, the folds 29 and spaces that are formed between the folds 29 are maintained. As shown in FIGS. 3 and 6, the folds 29 formed by the outer sheet 22 are portions that are caused to protrude toward the non-skin-facing surface side in the thickness direction Z of the outer sheet 22 due to contraction of the elastic members 24, whereas the folds 29 formed by the inner sheet 23 are portions that are caused to protrude toward the skin-facing surface side in the thickness direction Z of the inner sheet 23 due to contraction of the elastic members 24. Moreover, in the thickness direction Z of the outer sheet 22, recessed portions that are located between the folds 29 are also referred to as groove portions 29b. As shown in FIGS. 3 and 6, in light of tactile feel, it is preferable that the top portions of protruding portions of the respective folds 29 are circular-arc-shaped in cross section.

Figure 4:
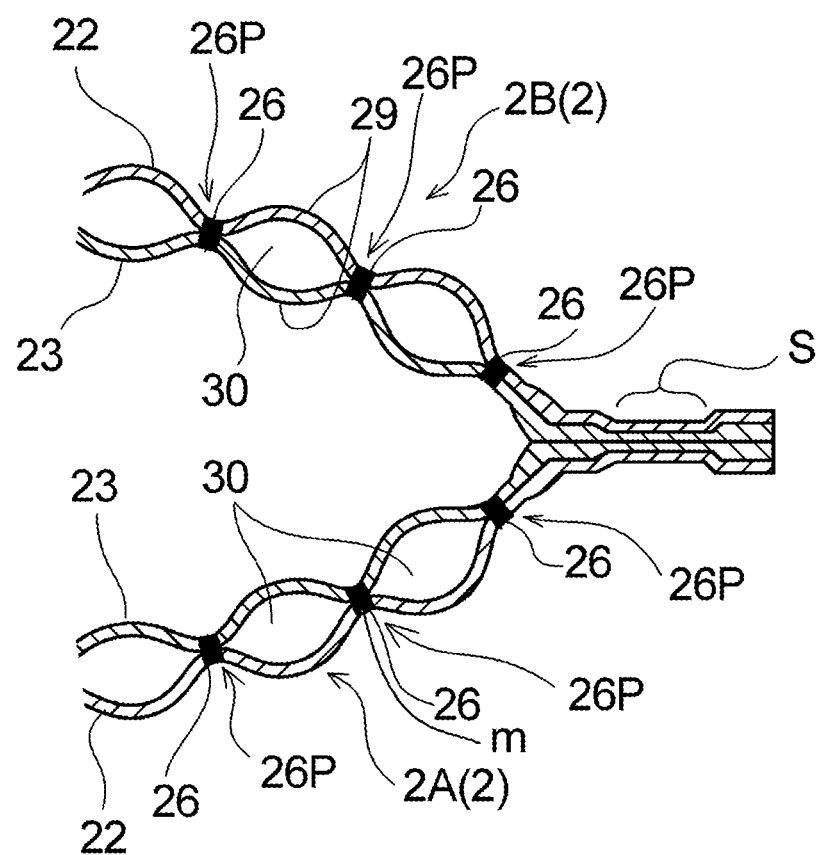
FIG. 4 is an enlarged cross-sectional view showing a cross section of a below-waist lower elasticized portion of the diaper shown in FIG. 1 taken in an article lateral direction.
Figure 5:
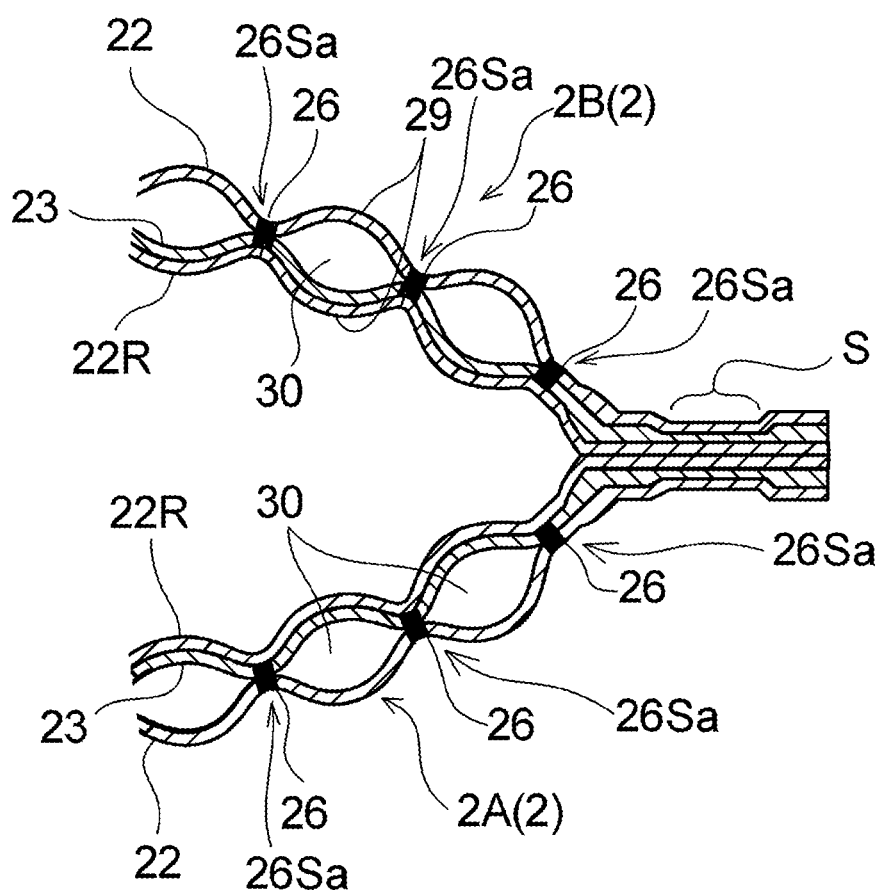
FIG. 5 is an enlarged cross-sectional view showing a cross section of a waist elasticized portion of the diaper shown in FIG. 1 taken in the article lateral direction.

In the diaper 1 of the present embodiment, as shown in FIG. 4, in the below-waist lower elasticized portions G2 of each of the front portion A and the rear portion B, the two sheets 22 and 23 are joined to each other at the joined regions 26 so as to form the hollow portions 30. Moreover, in the diaper 1 of the present embodiment, the sheet material composing the outer sheet 22 of each of the front portion A and the rear portion B is folded back onto a skin-facing surface side of the inner sheet 23 along a circumferential edge portion 51 of the waist opening 5, and this folded-back portion 22R covers the skin-facing surface side of the inner sheet 23 in the waist elasticized portion G1 (see FIG. 5). Moreover, the folded-back portion 22R is joined to a skin-facing surface of either the inner sheet 23 or the absorbent assembly 3 or both with an adhesive applied to the entirety or a portion of a surface of the folded-back portion 22R, but is not fusion-bonded to the joined regions 26. Thus, the joined regions 26 may also be joined regions at which the three layers, that is, the outer sheet 22, the inner sheet 23, and the folded-back portion 22R are integrated through hot embossing.

Figure 3A:
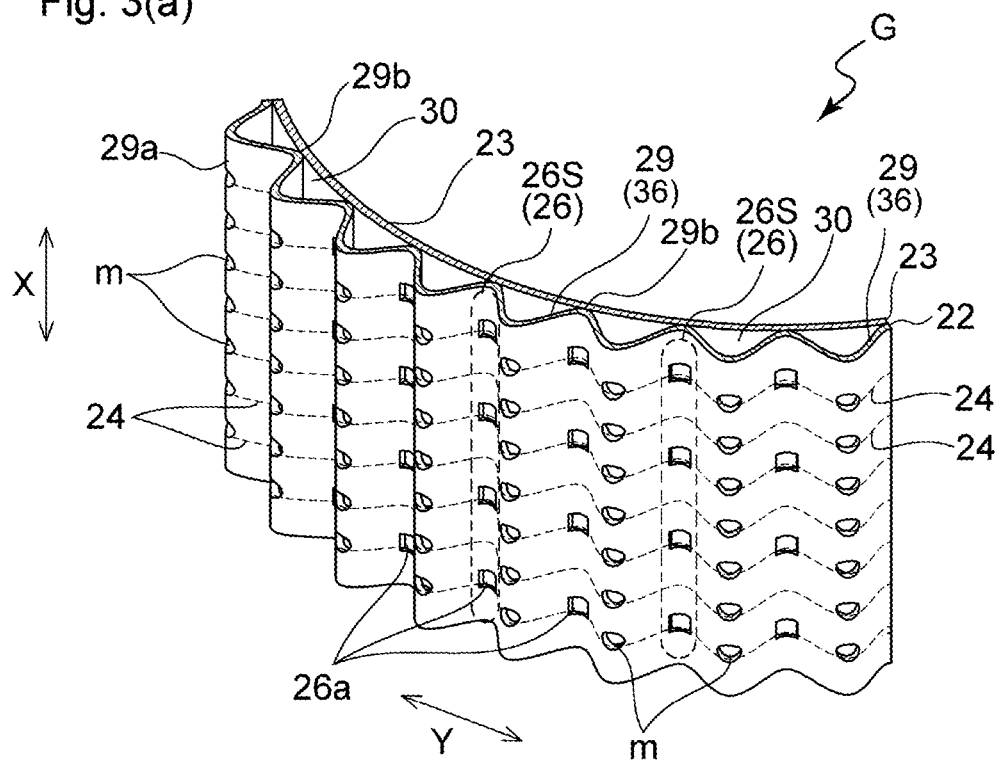
FIGS. 3(a) and 3(b) are a perspective view and a schematic plan view, respectively, showing an elasticized portion of the diaper shown in FIG. 1.
Figure 3B:
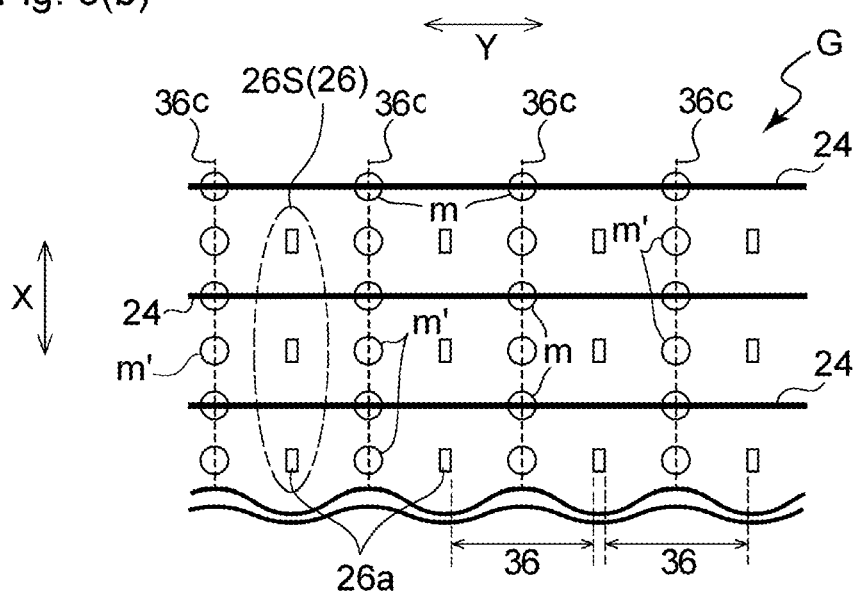

In the outer sheet 22, as shown in FIGS. 3(a) and 3(b), holes m are formed in the above-described folds 29 in the elasticized portion G so as to overlap the elastic members 24. The holes m are formed in sections of the folds 29 other than the joined regions 26. That is to say, the holes m are formed in the non-joined regions 36.

Although the diaper 1 of the present embodiment has the holes m that are formed so as to overlap the elastic members 24 in the waist elasticized portions G1 and the below-waist lower elasticized portions G2, it is sufficient that the outer sheet 22 has holes m that are formed at positions overlapping the elastic members 24 in the thickness direction in at least either the waist elasticized portion G1 or the below-waist lower elasticized portions G2, which are the regions where the elastic members 24 are arranged. In the following description, the "holes m that are formed at positions overlapping the elastic members 24 in the thickness direction" will also be referred to as the "holes m that overlap the elastic members 24".

FIG. 3(b) is a plan view of the elasticized portion G in a stretched state in which the elastic members 24 are stretched in the article lateral direction Y, that is, an uncontracted state of the elastic members 24. In the diaper 1 of the present embodiment, as shown in FIG. 3(b), both holes m that overlap the elastic members 24 and holes m' that do not overlap the elastic members 24, or only the holes m that overlap the elastic members 24, may be formed in the elasticized portion G. Whether or not a hole m is formed at a position overlapping an elastic member 24 is judged in a state in which the elastic members 24 are stretched in the article lateral direction Y.

Figure 8A:
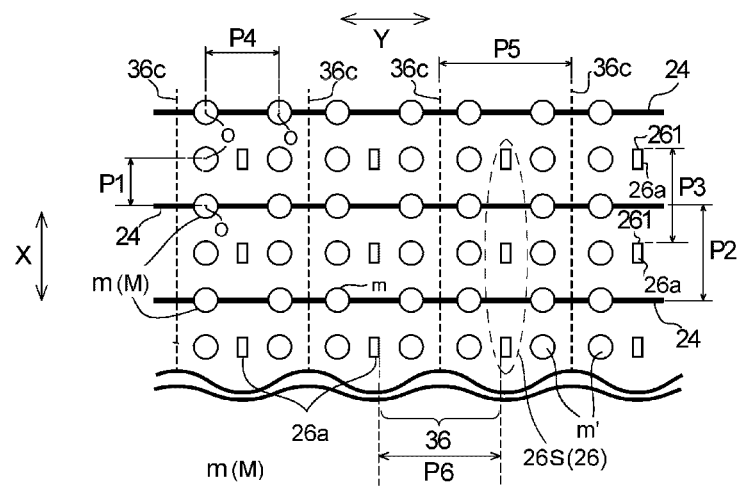
FIGS. 8(a) to 8(c) are plan views showing arrangement relationships of holes, elastic members, joined regions, and folds in the elasticized portion according to the present invention.
Figure 8B:
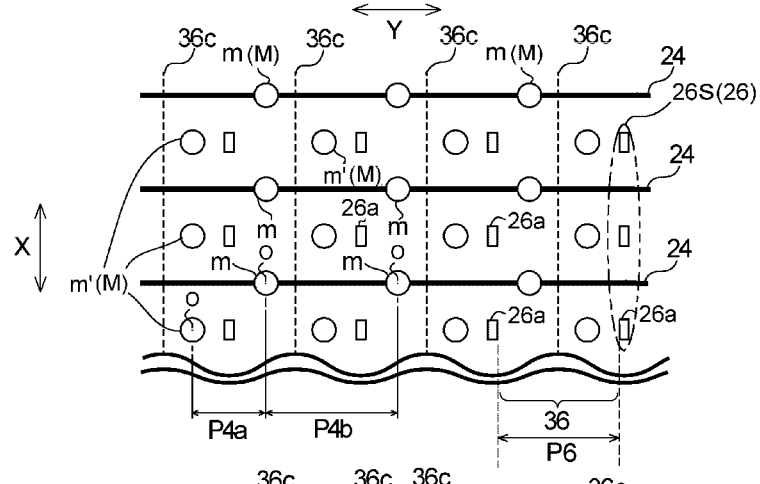
Figure 8C:
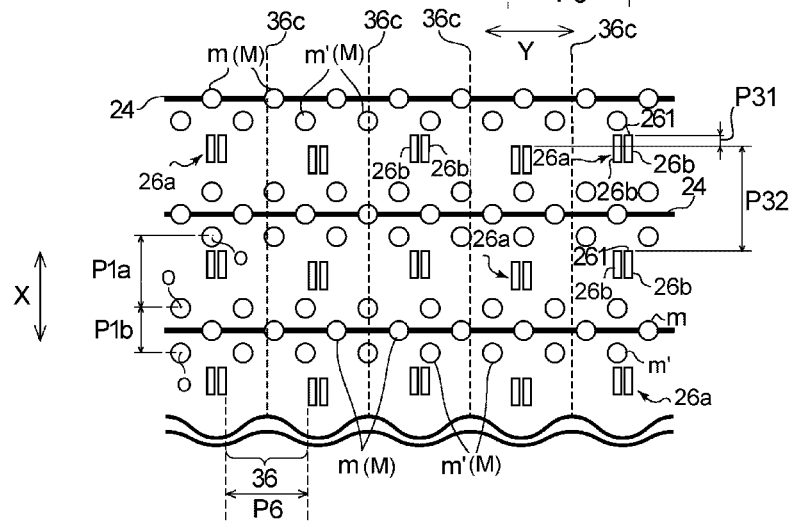

Moreover, in the diaper 1 of the present embodiment, as shown in FIG. 3(b), the holes m overlap center lines 36c that pass through the centers of the respective non-joined regions 36, where the folds 29 are formed, in the article lateral direction Y. The center line 36c portions are lines that bisect the width of the respective non-joined regions 36 in the article lateral direction Y and substantially coincide with the top portions of the folds 29. The top portions of the folds 29 are portions that protrude the farthest in the thickness direction Z of the individual folds 29. Although the holes m of the present embodiment are formed so as to overlap the above-described center lines 36c, the holes m may also be formed at positions that do not overlap the center lines 36c of the non-joined regions 36 as shown in FIGS. 8(a) to 8(c), which will be described later. In the case where non-joined regions 36 each continuously extend in the article lateral direction Y. and folds 29 each extending in the article lateral direction Y are formed, the center lines 36c of the non-joined regions 36 are the lines that bisect the width of the respective non-joined regions 36 in the article longitudinal direction X.

As shown in FIG. 6, the holes m in the outer sheet 22 of the present embodiment penetrate the outer sheet 22. Moreover, individual holes m and an elastic member 24 with which the holes m overlap in a plan view overlap in the thickness direction Z as shown in FIG. 6. The cross-sectional area of each hole m of the present embodiment in a direction that is perpendicular to the thickness direction Z continuously decreases from the non-skin-facing surface side toward the skin-facing surface side. As described above, the holes m are formed at positions that overlap portions of the elastic members 24, but it is sufficient that skin-facing surface-side openings m2 of the individual holes m entirely or partially overlap the elastic members 24.

The joined regions 26 of the diaper 1 of the present embodiment are formed by a joined region forming step in which the outer sheet 22 and the inner sheet 23 are placed one on top of the other, and the resulting laminated portion is subjected to hot embossing. The holes m are formed by performing hole making processing in sections of the two sheets 22 and 23 other than the joined regions 26 that have been formed in the joined portion forming step.

In the joined region forming step, for example, a hot embossing apparatus including an embossing roller and an anvil roller and having, on an outer circumferential surface of the embossing roller, joining projections whose leading end surfaces have a similar shape to the outline of the joined regions 26 can be used. In the case where the longitudinal joined regions 26 intermittently extend in the article longitudinal direction X, for example, it is possible to use a hot embossing apparatus that has joining projections that have a similar shape to the outline of the intermittent joined regions 26a, which constitute the joined regions 26 and are intermittently formed in the article longitudinal direction X. In the case where the joined regions 26 continuously extend in the article longitudinal direction X, for example, it is possible to use a hot embossing apparatus that has joining projections that continuously extend in the article longitudinal direction X in a similar manner to the outline of the joined regions 26. To perform the hole making processing, for example, a cutting apparatus including a cutter roller and an anvil roller and having, on an outer circumferential surface of the cutter roller, cutting blades having a shape corresponding to the outline of the holes m can be used.

In the diaper 1 of the present embodiment, the joined regions 26 are formed by performing the joined region forming step on the outer sheet 22 and the inner sheet 23 that are placed one on top of the other so as to sandwich the elastic members 24. In the outer sheet 22, the holes m have been formed through the hole making processing at a stage before the joined region forming step is performed.

The diaper 1 can be worn in a similar manner to an ordinary pull-on disposable diaper.

Figure 6A:
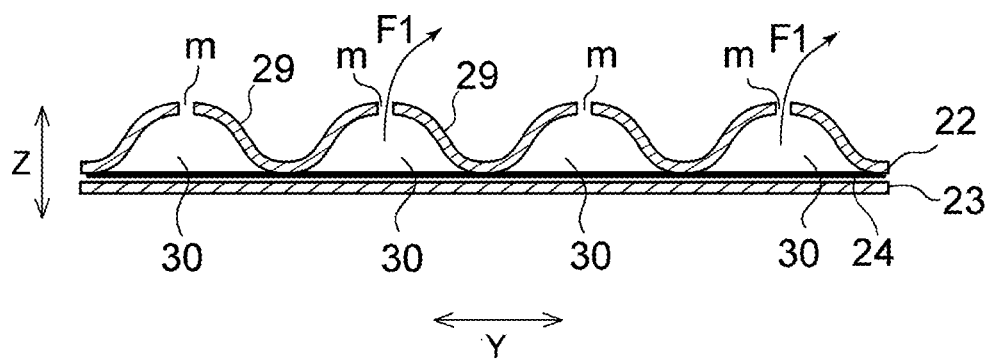
FIGS. 6(a) and 6(b) are enlarged cross-sectional views showing a cross section of the elasticized portion shown in FIG. 3 taken in a thickness direction.
Figure 6B:
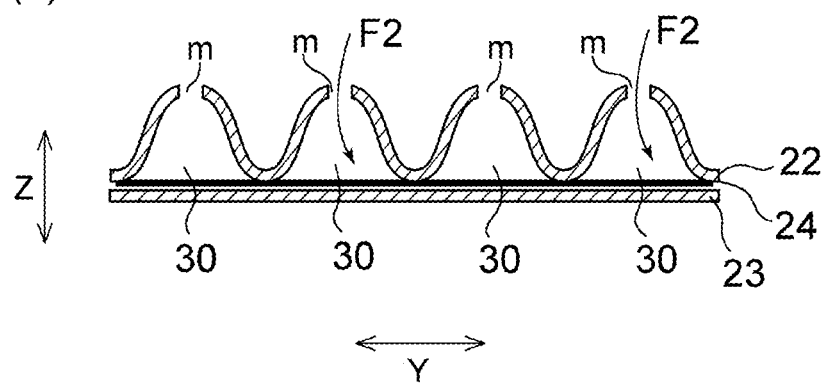

In the diaper 1 of the present embodiment, when the wearer performs a movement such as standing up or sitting down, the elastic members 24 are stretched or contract, and accordingly, the hollow portions 30 inside the folds 29 in the elasticized portion G expand or shrink in the thickness direction Z of the elasticized portion G as shown in FIGS. 6(a) and 6(b). More specifically, if the elastic members 24 are stretched, the space of each of the hollow portions 30 inside the folds 29 formed in the outer sheet 22 shrinks as shown in FIG. 6(a), and if the elastic members 24 contract, the space of each of the hollow portions 30 inside the folds 29 formed in the outer sheet 22 expands as shown in FIG. 6(b). The expansion or shrinkage of the hollow portions 30 may also be caused by a change in pressure that is applied from the non-skin-facing surface side of the diaper 1 when the diaper 1 is worn, such as the pressure applied from a garment or the like disposed on the outside of the diaper 1.

When the hollow portions 30 inside the folds 29 expand or shrink, flows F1 or F2 of air flowing into or out of the hollow portions 30 are generated because the folds 29 formed by the outer sheet 22 have the holes m, and thus, ventilation of the hollow portions 30 is promoted. That is to say, as shown in FIG. 6(a), if the spaces of the respective hollow portions 30 shrink, the flows F1 of air in the hollow portions 30 being discharged to the outside via the holes m are generated, whereas as shown in FIG. 6(b), if the spaces of the respective hollow portions 30 expand, the flows F2 of outside air flowing into the hollow portions 30 via the holes m are generated. In the following description, this effect will also be referred to as the "bellows effect". In the diaper 1, the hollow portions 30 of the folds 29 extending in the article longitudinal direction X serve as ventilation paths, air in the hollow portions 30 is ventilated by the above-described bellows effect, moisture in the hollow portions 30 and moisture in the diaper 1 when worn are easily allowed to efficiently escape to the outside, and thus the occurrence of trapping of heat and moisture and the like can be suppressed.

Furthermore, although the inner sheet 23 is pressed by the elastic members 24 when the diaper is worn, and the breathability of the pressed sections is likely to deteriorate, the breathability of the elastic member arrangement sections, where the breathability is likely to deteriorate, can be improved by providing the outer sheet 22 with the holes m that overlap the elastic members 24 as in the present invention, that is, by providing the holes m at sections corresponding to the sections pressed by the elastic members 24 and thereby positively performing ventilation. Moreover, in the elastic member arrangement sections, spaces are likely to be maintained between the outer sheet 22 and the elastic members 24 that press the inner sheet 23 toward the skin-facing surface side, and therefore, the above-described bellows effect is even more reliably achieved by providing the holes m at positions overlapping the elastic members 24. With the above-described effects, the absorbent article of the present invention has excellent breathability.

It should be noted that in the case where holes are provided in the inner sheet 23 at positions overlapping the elastic members 24, the holes may be blocked by the elastic members 24 or the holes may be blocked by the inner sheet 23 being twisted due to contraction of the elastic members 24, and it is therefore not possible to achieve the expected improvement in the breathability.

Furthermore, in the elasticized portion G of the diaper 1 of the present embodiment, the joined regions 26 are intermittently formed in the article longitudinal direction X. In addition, the elastic members 24 are arranged between the joined regions 26 adjacent to one another in the article longitudinal direction X, and the elastic members 24 are not fastened to the sheets 22 and 23 in the joined regions 26. Thus, with the folds 29 that are formed by the sheet 22 or the sheet 23, the outer cover 2 deforms even more flexibly in accordance with a load that is applied in the thickness direction, and thus has an even more excellent tactile feel and the like.

With respect to each of the holes m provided in the outer sheet 22 of the diaper 1, the opening diameter of a non-skin-facing surface-side opening m1 and the opening diameter of a skin-facing surface-side opening m2 are different from each other. It is preferable that the non-skin-facing surface-side opening m1 of each hole m is larger than the skin-facing surface-side opening m2 thereof. With this configuration, a favorable tactile feel is perceived when touching the non-skin-facing surface side of the outer sheet 22. Furthermore, with the above-described configuration, the thickness of each hole m and its circumferential edge is smaller than that of sections other than the holes m, and the space of the hollow portion 30 decreases in that hole m.

Therefore, heat and moisture are easily discharged from the hollow portions 30 of the folds 29, and a high ventilation efficiency is achieved even when the holes are small. Since the holes m are recessed toward the skin side of the outer sheet 22, that is, the non-skin-facing surface-side openings m1 of the holes are larger than the skin-facing surface-side openings m2, the effect of making it even easier for heat and moisture in the hollow portions 30 of the folds 29 to be discharged without being accumulated therein can be achieved.

FIGS. 7(a) to 7(d) are diagrams showing variations of the form of the holes m according to the present invention.

Figure 7A:
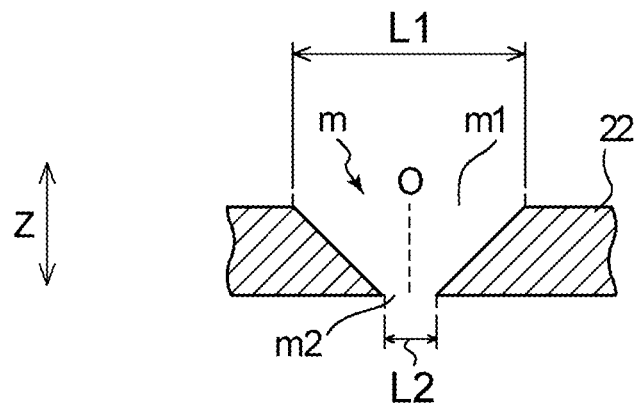
FIGS. 7(a) to 7(d) are enlarged cross-sectional views showing variations of a hole according to the present invention.

With respect to the hole m shown in FIG. 7(a), the cross-sectional area in a direction that is perpendicular to the thickness direction Z continuously decreases from the non-skin-facing surface side toward the skin-facing surface side. Inward of an outer circumferential edge of the hole m, the thickness of this outer sheet 22 continuously decreases toward a center portion O of that hole in a plan view. With this configuration, if the skin of a hand or the like comes into contact with this hole portion, a favorably smooth tactile feel that does not cling to the skin is perceived, and heat and moisture in the hollow portions 30 of the folds 29 are even more easily discharged without being accumulated therein. Thus, it is preferable that the outer sheet 22 has, inward of the outer circumferential edge of each hole m, a portion in which the thickness gradually decreases toward the center portion O of the hole m. It should be noted that, in the outer sheet 22, "inward of the outer circumferential edge of each hole m" refers a portion that is closer to the center portion O of the hole m than the outer circumferential edge of the non-skin-facing surface-side opening m1 of the hole m is. The center portion O of a hole m is the center of the skin-facing surface-side opening m2 thereof in a plan view. The position of the center portion O of the hole m shown in FIG. 7(a) coincides with the position of the central axis of the hole m in a plan view.

Figure 7B:
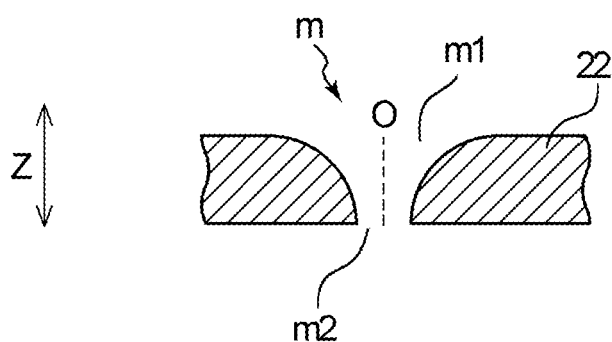

As a form in which the outer sheet 22 has, inward of the outer circumferential edge of each hole, a portion in which a thickness of the outer sheet 22 gradually decreases toward the center portion O of the hole m, as shown in FIG. 7(a), the hole m may be formed to have a straight outline in cross sections taken in the thickness direction Z of the outer sheet 22. Moreover, as shown in FIG. 7(b), the hole m may also be formed to have a curved outline in cross sections taken in the thickness direction Z.

Figure 7C:
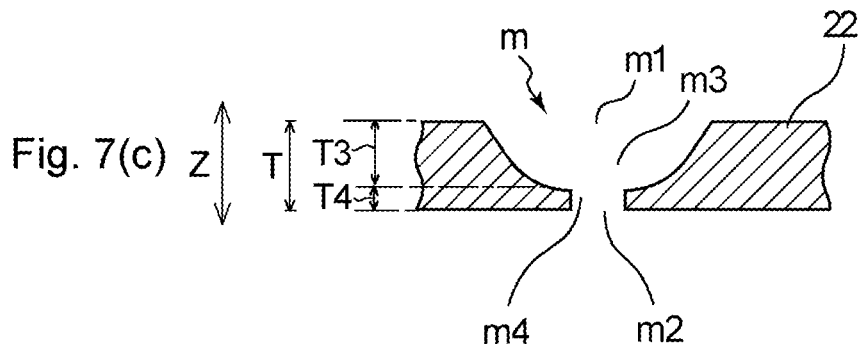

A hole m shown in FIG. 7(c) has, in a cross section taken in the thickness direction Z, a depressed portion m3 that is curved into a bowl shape and a communication portion m4 that is located closer to the skin-facing surface side than the depressed portion m3 is. The communication portion m4 is a portion having a constant cross-sectional area in the direction that is perpendicular to the thickness direction Z. Since the hole m has the depressed portion m3 and the communication portion m4, the communication portion m4 of the hole m makes it possible to, while maintaining the favorable tactile feel, even further improve the strength of the circumferential edge portion of the skin-facing surface-side opening m2, where the strength of the outer sheet 22 is the weakest, and therefore to even more effectively prevent breakage or splitting of the outer sheet 22 starting at the hole m from occurring during the production of the absorbent article or when the wearer puts on the absorbent article. Thus, it is preferable that each hole m has the depressed portion m3, in which the cross-sectional area of the hole in the direction that is perpendicular to the thickness direction gradually decreases toward the skin-facing surface side, and the communication portion m4, which is located closer to the skin-facing surface side than the depressed portion m3 is and in which the cross-sectional area in the direction that is perpendicular to the thickness direction is constant.

From the standpoint of even more effectively achieving the above-described effects, the thickness T4 of the communication portion m4 in the thickness direction Z of the outer sheet 22 is preferably 5% or greater, and more preferably 10% or greater, is preferably 80% or less, and more preferably 70% or less, and is preferably from 5% to 80% and more preferably from 10% to 70%, with respect to the total thickness T of the depressed portion m3 and the communication portion m4.

It should be noted that the thickness T3 of the depressed portion m3 and the thickness T4 of the communication portion m4 are measured in a state (uncontracted state) in which the elasticized portion G is stretched in the article lateral direction.

Although the total thickness T of the depressed portion m3 and the communication portion m4 shown in FIG. 7(c) is the sum of the thickness T3 of the depressed portion m3 and the thickness T4 of the communication portion m4, the thickness of the hole m shown in FIG. 7(c) is equal to the thickness of a section of the outer sheet 22 other than the sections where the holes m are formed.

Figure 7D:
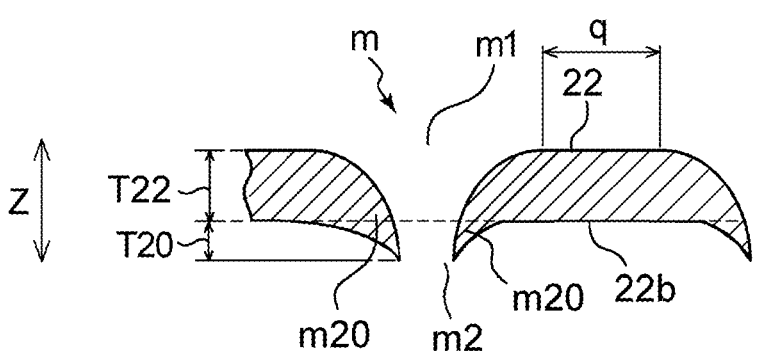

A hole m shown in FIG. 7(d) is formed so that, in a cross section taken in the thickness direction Z, the outline of the hole m is curved, and an edge m20 of the skin-facing surface-side opening m2 protrudes toward the skin-facing surface side. With this configuration, in the non-joined regions, spaces are easily formed between the inner sheet 23 and the outer sheet 22, the hollow portions 30 of the folds 29 are easily formed, and a high ventilation efficiency is achieved. Thus, it is preferable that in each hole m, the circumferential edge portion m20 of the skin-facing surface-side opening m2 protrudes farther toward the skin-facing surface side than the position of a skin-facing surface 22b of a section q of the outer sheet 22 other than the holes m. This protruding portion will also be referred to as the circumferential edge protruding portion m20. In the hole m shown in FIG. 7(d), the skin-facing surface-side opening m2 is located closer to the skin-facing surface side than the skin-facing surface 22b of the outer sheet 22 is.

From the standpoint of even more reliably achieving the above-described effects, it is preferable that the thickness T20 of the circumferential edge protruding portion m20 is smaller than the thickness T22 of the outer sheet 22. Moreover, from a similar standpoint, the thickness T20 of the circumferential edge protruding portion m20 is preferably 5% or greater, and more preferably 10% or greater, is preferably 80% or less, and more preferably 70% or less, and is preferably from 5% to 80% and more preferably from 10% and 70%, with respect to the thickness T22 of the outer sheet 22. Here, the thickness T22 of the outer sheet 22 is the thickness of the section q of the outer sheet 22 other than the holes m. The section q of the outer sheet 22 other than the holes m is a section of the outer sheet 22 that does not overlap any hole m in a plan view.

The thickness T20 of the circumferential edge protruding portion m20 and the thickness T22 of the outer sheet 22 are measured in a state (uncontracted state) in which the elasticized portion G is stretched in the article lateral direction.

In the outer sheet 22 that has the hole m shown in any of FIGS. 7(a) to 7(d), the inter-fiber distance in a portion of the hole m inward of the outer circumferential edge thereof continuously decreases inward in the hole m, that is, toward the center portion O of the hole in a plan view. That is to say, the fiber density in the portion of the hole m inward of the outer circumferential edge thereof continuously increases inward in the hole m, that is, toward the center portion O of the hole in a plan view. In this outer sheet 22, gaps between the fibers in the portion of the hole m inward of the outer circumferential edge thereof are smaller than those in the section other than the holes m.

From the standpoint of allowing the hole shape to be maintained even when pressure is applied, it is preferable that the inter-fiber distance in the circumferential edge portion of each hole m of the outer sheet 22 is smaller than the inter-fiber distance in a section of the outer sheet 22 other than the holes m. Moreover, it is preferable that the fiber density in the circumferential edge portion of each hole m of the outer sheet 22 is higher than the fiber density in a section of the outer sheet 22 other than the holes m.

The inter-fiber distance in the circumferential edge portion of a hole m and the inter-fiber distance in a section other than the holes m are measured using the following method.

Method for Measuring Inter-Fiber Distance

The basis weight, the thickness, and the fiber denier of a measurement portion of a sheet are measured, and the inter-fiber distance is calculated according to an equation (1) below. When different portions of a sheet such as the outer sheet 21 in which the holes m are provided are measured, the basis weight and the fiber denier of the sheet do not change, but the thickness changes depending on the measurement portions.

The thickness is measured as follows. To measure the thickness of the sheet, a measurement target portion including the circumferential edge portion of a hole m or a section other than the holes m is cut in the thickness direction such that the cut face of the measurement target portion does not collapse. A knife, a cutter, a razor, or the like is used to cut the measurement target portion. Then, the cut cross-section is observed using a microscope, and the thickness of the measurement portion is measured. The thickness is measured at ten different points in the cut measurement target portion, and an average thereof is calculated as the thickness of the measurement portion.

It should be noted that the basis weight is calculated from the weight of the measured portion of the sheet and the lengths thereof in the longitudinal direction and the lateral direction. The fiber denier is the weight per length of 9,000 m of a fiber, and can be obtained from the specific gravity (substantially the density) of fibers and the cross-sectional area of the fibers. In the case where fibers of each of the sheets are constituted by a single type of fiber, the resin used in the fibers is identified using DSC. In the case of a composite fiber, such as a composite fiber having a core-sheath structure, the sheath component is the fusion-bondable component, and therefore, identification of the resin is performed in a similar manner using DSC, and the fiber denier is obtained by calculating an average specific gravity based on a cross section when magnified and observed. In the case where a plurality of types of fibers are used, an average specific gravity is calculated based on the mixing ratio of the fibers.

$$\text{Inter-fiber distance } (\mu m) = 10^4 \sqrt{\frac{10L}{9w} \cdot \left[\frac{1}{\sum_{i=1}^{p} \frac{\alpha i}{Di}}\right]} \quad (1)$$

where L represents the thickness (cm) of a sheet (outer sheet), w represents the basis weight (g/m$^2$) of the sheet, Di represents the fiber denier of a constituent fiber i constituting the sheet, and αi represents the weight proportion (%) of the constituent fiber i.

In the present embodiment, although the holes m are formed in the folds 29 formed by the outer sheet 22 so as to overlap the elastic members 24, it is sufficient that the holes provided in the folds 29 partially overlap the elastic members 24. It is sufficient that at least one hole m is arranged so as to overlap an elastic member 24, but it is preferable that a plurality of holes m are arranged so as to overlap elastic members 24.

Moreover, in the present embodiment, the holes m are formed in the folds 29 in the waist elasticized portions G1 and the below-waist lower elasticized portions G2 so that the holes m overlap the elastic members 24. Since a waist portion is a section that easily sweats, from the standpoint of even further improving the breathability of the diaper 1, a circumferential edge end 5a of the waist opening 5 is formed by an end portion Sal of the front panel 2A and an end portion 5a2 of the rear panel 2B in the article longitudinal direction X. The end portion 5al of the front panel 2A is also referred to as a front end portion Sal of the outer cover, and the end portion 5a2 of the rear panel 2B is also referred to as a rear end portion 5a2 of the outer cover. Moreover, with regard to both end portions of the absorbent assembly 3 in the longitudinal direction X, the end portion on the rear side is also referred to as a rear end portion 3b, and the end portion on the front side is also referred to as a front end portion 3a. A region G1 spanning between the rear end portion 5a2 of the outer cover and the rear end portion 3b of the absorbent assembly 3, or a region G1 spanning between the front end portion Sal of the outer cover and the front end portion 3a of the absorbent assembly 3, the number of holes m that overlap the elastic members 24 is preferably 5% or greater, and more preferably 8% or greater, is preferably 80% or less, and more preferably 70% or less, and is preferably from 5% to 80% and more preferably from 8% to 70%, with respect to the total number of holes in that region G1. It is preferable that the region G1 in either of the front panel 2A or the rear panel 2B of both has this configuration. It should be noted that the waist elasticized portions G1 of the present embodiment correspond to the above-described regions G1. It should also be noted that the total number of holes in a region G1 is the number of all the holes that are present in that region G1 of the outer sheet 22, and the total number includes the holes that overlap the elastic members 24 and the holes that do not overlap the elastic members 24. Although the holes shown in FIG. 2 are formed in the folds 29 between the joined regions 26 adjacent to one another in the article lateral direction Y, the total number of holes in each region G1 includes holes that are formed in the folds 29 and holes that are formed in sections other than the folds 29.

In light of the improvement in breathability, the tactile feel, and the strength of the outer sheet 22, the area of the non-skin-facing surface-side opening m1 of each hole m is preferably 110% or greater, and more preferably 120% or greater, is preferably 500% or less, and more preferably 400% or less, and is preferably from 110% to 500% and more preferably from 120% to 400%, with respect to the area of the skin-facing surface-side opening m2.

In light of the improvement in breathability and the strength of the outer sheet 22, the area of the skin-facing surface-side opening m2 of each hole m is preferably 0.1 mm$^2$ or greater, and more preferably 0.2 mm$^2$ or greater, is preferably 9 mm$^2$ or less, and more preferably 7 mm$^2$ or less, and is preferably from 0.1 to 9 mm$^2$ and more preferably from 0.2 to 7 mm$^2$.

The areas of the skin-facing surface-side opening m2 and the non-skin-facing surface-side opening m1 of a hole m are measured in a state (uncontracted state) in which the elasticized portion G is stretched in the article lateral direction.

In light of the improvement in breathability, the tactile feel, and the strength of the outer sheet 22, the opening diameter L1 of the non-skin-facing surface-side opening m1 of each hole m is preferably 110% or greater, and more preferably 120% or greater, is preferably 300% or less, and more preferably 200% or less, and is preferably from 110% to 300% and more preferably from 120% and 200%, with respect to the opening diameter L2 of the skin-facing surface-side opening m2.

The area of the non-skin-facing surface-side opening m1 of a hole m is measured in a state (uncontracted state) in which the elasticized portion G is stretched in the article lateral direction.

It should be noted that with regard to the opening diameters L1 and L2 of the holes m according to the present invention, in the case where the shape of the non-skin-facing surface-side opening m1 or the skin-facing surface-side opening m2 is an ellipse, the length of the major axis of the ellipse is used as the opening diameter L1 or L2. Moreover, in the case where the shape of the non-skin-facing surface-side opening m1 or the skin-facing surface-side opening m2 is a shape other than a circle and an ellipse, the equivalent circle diameter based on the area of the opening m1 or m2 is used as the opening diameter L1 or L2 of the hole m.

In light of the improvement in breathability and the strength of the absorbent article, in each of the front panel 2A and the rear panel 2B, the total area of the holes m in the waist elasticized portion G1 is preferably 2% or greater, and more preferably 4% or greater, is preferably 30% or less, and more preferably 25% or less, and is preferably from 2% to 30% and more preferably from 4% to 25%, with respect to the area of the waist elasticized portion G1. It should be noted that if the area of the non-skin-facing surface-side opening m1 of a hole m is different from the area of the skin-facing surface-side opening m2 of that hole m, the area of the smaller opening is used as the area of that hole m.

In light of the strength of the outer sheet 22 and the improvement in breathability, in each of the front panel 2A and the rear panel 2B, the total area of the holes m in the below-waist lower elasticized portions G2 is preferably 2% or greater, and more preferably 4% or greater, is preferably 30% or less, and more preferably 25% or less, and is preferably from 2% to 30% and more preferably from 4% to 25%, with respect to the area of the below-waist lower elasticized portions G2.

The total area of the holes m in the waist elasticized portion G1 and the total area of the holes m in the below-waist lower elasticized portions G2 are each measured in a state (uncontracted state) in which the elasticized portion G is stretched in the article lateral direction. Moreover, the total area of the holes is the total area of all the holes that are present in the waist elasticized portion G1 of the outer sheet 22, and includes the holes that overlap the elastic members 24 and the holes that do not overlap the elastic members 24. Although the holes shown in FIG. 2 are formed in the folds 29 between the joined regions 26 adjacent to one another in the article lateral direction Y, the above-described total area of the holes includes the holes that are formed in the folds 29 and the holes that are formed in sections other than the folds 29.

In light of the strength of the outer sheet 22 and the improvement in breathability, the opening diameter L2 of the skin-facing surface-side opening m2 of each hole m is preferably 0.5 mm or greater, and more preferably 0.7 mm or greater, is preferably 3 mm or less, and more preferably 2 mm or less, and is preferably from 0.5 to 3 mm and more preferably from 0.7 and 2 mm. The opening diameter L2 of the skin-facing surface-side opening m2 of a hole m is measured in a state (uncontracted state) in which the elasticized portion G is stretched in the article lateral direction.

FIGS. 8(a) to 8(c) are diagrams each showing an arrangement relationship of the holes m, the joined regions 26, the elastic members 24, and portions constituting the folds 29 in a stretched state in which the elastic members 24 are stretched in the article lateral direction Y, that is, an uncontracted state of the elastic members 24. FIGS. 8(a) to 8(c) show the center lines 36c that pass through the centers of the respective non-joined regions 36 in the article lateral direction Y as the portions constituting the folds 29. The center lines 36c are the lines that bisect the respective folds 29 in the article lateral direction Y, and are portions that protrude the farthest in the thickness direction of the outer sheet 22 when the folds 29 are formed.

Moreover, in FIGS. 8(a) to 8(c), the joined region rows 26S are formed in each of which a plurality of intermittent joined regions 26a that are intermittently formed in the article longitudinal direction X are lined up in a straight line. Furthermore, in FIGS. 8(a) to 8(c), the holes m that overlap the elastic members 24 and the holes m' that do not overlap the elastic members 24 are both present. In the following description, the holes m that overlap the elastic members 24 and the holes m' that do not overlap the elastic members 24 will also be collectively referred to as "holes M".

The holes M may be formed in the same pattern or in different patterns.

The wording "the same pattern" as used herein means an embodiment in which the holes M have the same shape and the same size in terms of their form and the holes M are arranged in the same manner. For example, the holes M shown in FIG. 8(a) have the same shape and the same size and are arranged at regular intervals in each of the article longitudinal direction X and the article lateral direction Y. That is to say, the holes M shown in FIG. 8(a) are arranged with a predetermined pitch P1 in the article longitudinal direction X and also arranged with a predetermined pitch P4 in the article lateral direction Y.

As shown in FIG. 8(a), the pitch P1 of the holes in the article longitudinal direction X is the minimum distance between the centers of the holes M in the article longitudinal direction X. As shown in FIG. 8(a), the pitch P4 of the holes in the article lateral direction Y is the minimum distance between the centers of the holes M in the article lateral direction Y. It should be noted that as shown in FIG. 8(c), the pitch P1 of the holes in the article longitudinal direction X includes a case where it is the minimum distance P1b between the centers of the holes M that are located at the same position in the article lateral direction Y and a case where it is the minimum distance P1a between the centers of the holes M that are located at different positions in the article lateral direction Y. As shown in FIG. 8(b), the pitch P4 of the hole in the article lateral direction Y includes a case where it is the minimum distance P4b between the holes M that are located at the same position in the article longitudinal direction X and a case where it is the minimum distance P4a between the holes M that are located at different positions in the article longitudinal direction X.

The wording "different patterns" as used herein includes a case where only the form of the holes M varies, a case where only the arrangement of the holes M varies, and a case where both the form and the arrangement vary.

An embodiment in which the form of the holes M varies also includes a case where the holes M have different shapes in a plan view. An example of the embodiment in which the form of the holes M varies is an embodiment in which holes M having a circular shape and holes M having another shape such as a square shape or an oblong shape are both present.

An embodiment in which the arrangement of the holes M varies includes a case where the holes M are arranged with different pitches in the article longitudinal direction X, a case where the holes M are arranged with different pitches in the article lateral direction Y, and a case where the holes M are arranged with different pitches in both of these directions.

For example, as shown in FIG. 8(b), the holes M may be regularly arranged with two types of pitches P4a and P4b in the article lateral direction Y. The holes M shown in FIG. 8(b) are intermittently arranged in the article lateral direction Y so as to alternatingly have the two types of pitches P4a and P4b in the article lateral direction Y. In the case where the holes M are arranged with different pitches in the article lateral direction Y in this manner, an average of the plurality of types of pitches P4a and P4b of the holes in the article lateral direction Y is used as the pitch P4 of the holes in the article lateral direction Y.

Moreover, as shown in FIG. 8(c), for example, the holes M may also be regularly arranged with two types of pitches P1a and P1b in the article longitudinal direction X. The holes M shown in FIG. 8(c) are intermittently arranged in the article longitudinal direction X so as to alternatingly have the two types of pitches P1a and P1b in the article longitudinal direction X.

In the joined region rows 26S, which are the longitudinal joined regions 26, shown in FIGS. 8(a) to 8(c), the intermittent joined regions 26a that form the joined region rows 26S are formed to have the same shape and the same size. For example, the intermittent joined regions 26a shown in FIGS. 8(a) and 8(b) have an oblong shape, and the intermittent joined regions 26a shown in FIG. 8(c) are each constituted by two small oblong joined regions 26b being arranged side-by-side in the article lateral direction. The outline of the intermittent joined regions 26a in a plan view may also have other shapes such as a square shape, a circular shape, and an elliptical shape. Moreover, as shown in FIG. 8(c), the intermittent joined regions 26a may each be constituted by a plurality of small joined regions 26b. In this manner, the intermittent joined regions 26a may be formed in the same pattern, but may also be formed in different patterns. Moreover, the intermittent joined regions 26a may be formed in the same pattern, but may also be formed in different patterns.

The wording "the same pattern" as used herein means an embodiment in which the intermittent joined regions 26a that form the joined region rows 26S have the same shape and the same size in terms of their form, and the intermittent joined regions 26a are arranged in the same manner. For example, the plurality of intermittent joined regions 26a shown in FIG. 8(a) have the same shape and the same size. Moreover, the intermittent joined regions 26a shown in FIG. 8(a) are intermittently arranged at regular intervals in each of the article longitudinal direction X and the article lateral direction Y. Specifically, the joined regions 26 shown in FIG. 8(a) are arranged with a predetermined pitch P3 in the article longitudinal direction X. Moreover, the intermittent joined regions 26a are arranged with a predetermined pitch in the article lateral direction Y. As shown in FIG. 8(a), a plurality of intermittent joined regions 26a that are lined up along the article longitudinal direction X constitute a single joined region row 26S along the article longitudinal direction X. The joined region rows 26S are arranged with a predetermined pitch in the article lateral direction Y. In FIG. 8(a), the pitch of the intermittent joined regions 26a in the article lateral direction Y and the pitch of the joined region rows 26S in the article lateral direction Y match.

As shown in FIG. 8(a), the pitch P3 of the intermittent joined regions 26a in the article longitudinal direction X is the distance from an upper end 261 of an intermittent joined region 26a to an upper end 261 of another intermittent joined region 26a adjacent thereto in the article longitudinal direction X. The pitch P6 of the joined region rows 26S in the article lateral direction Y is the minimum distance from a side seal-side lateral end of an intermittent joined region 26a that constitutes a joined region row 26S to a side seal-side lateral end of an intermittent joined region 26a that constitutes another joined region row 26S adjacent to the former joined region row 26S in the article lateral direction Y.

The wording "different patterns" as used herein has a similar meaning to that of the above-described "different patterns" of the holes M. and also includes a case where only the form of the intermittent joined regions 26a varies, a case where only the arrangement of the intermittent joined regions 26a varies, and a case where both the form and the arrangement vary.

An embodiment in which the form of the intermittent joined regions 26a varies also includes a case where the intermittent joined regions 26a have different shapes in a plan view. An example of the embodiment in which the form of the intermittent joined regions 26a varies is an embodiment in which intermittent joined regions 26a having an oblong shape and intermittent joined regions 26a having a circular shape are both present.

An embodiment in which the arrangement of the intermittent joined regions 26a varies also includes a case where the intermittent joined regions 26a are arranged with different pitches P3 in the article longitudinal direction X or a case where the joined region rows 26S are arranged with different pitches P6 in the article lateral direction Y.

For example, as shown in FIG. 8(c), the intermittent joined regions 26a may be regularly arranged with two types of pitches P31 and P32 in the article longitudinal direction X. The intermittent joined regions 26a shown in FIG. 8(c) are intermittently arranged in the article longitudinal direction X so as to alternatingly have the two types of pitches P31 and P32 in the article longitudinal direction X.

In the case where a plurality of joined regions 26 each continuously extend in the article longitudinal direction X are formed in the article lateral direction Y, the joined regions 26 may be arranged with the same pitch or different pitches in the article lateral direction Y. In this case, the pitch of the joined regions in the article lateral direction Y is the distance from a side seal-side lateral end of a joined region 26 to a side seal-side lateral end of another joined region 26 adjacent to the former joined region 26 in the article lateral direction Y.

Moreover, from the standpoint of even more reliably achieving the above-described bellows effect, it is preferable that the pitch P1 of the holes in the article longitudinal direction X is equal to or smaller than the pitch P3 of the intermittent joined regions 26a in the article longitudinal direction X, as shown in FIG. 8(a). In the case where the holes M are arranged with different pitches in the article longitudinal direction X as shown in FIG. 8(c), the pitch P1 of the holes in the article longitudinal direction X is an average of the plurality types of pitches P1a and P1b of the holes in the article longitudinal direction X. Moreover, in the case where the intermittent joined regions 26a are arranged with different pitches in the article longitudinal direction X, the pitch P3 of the intermittent joined regions 26a in in the article longitudinal direction X is an average of the plurality types of pitches of the intermittent joined regions 26a in the article longitudinal direction X.

From a similar standpoint to that described above, the pitch P1 of the holes in the article longitudinal direction X is preferably 20% or greater, and more preferably 30% or greater, is preferably 90% or less, and more preferably 80% or less, and is preferably from 20% to 90% and more preferably from 30% to 80%, with respect to the pitch P3 of the intermittent joined regions 26a in the article longitudinal direction X.

From a similar standpoint to that described above, the pitch P1 of the holes in the article longitudinal direction X is preferably 1 mm or greater, and more preferably 2 mm or greater, is preferably 10 mm or less, and more preferably 8 mm or less, and is preferably from 1 to 10 mm and more preferably from 2 to 8 mm.

From a similar standpoint to that described above, the pitch P3 of the intermittent joined regions in the article longitudinal direction X is preferably 4 mm or greater, and more preferably 5 mm or greater, is preferably 10 mm or less, and more preferably 8 mm or less, and is preferably from 4 to 10 mm and more preferably from 5 to 8 mm.

It should be noted that the pitch P1 of the holes in the article longitudinal direction X and the pitch P3 of the intermittent joined regions 26a in the article longitudinal direction X are measured in a state (uncontracted state) in which the elasticized portion G is stretched in the article lateral direction.

From the standpoint of even more reliably achieving the above-described bellows effect, it is preferable that as shown in FIG. 8(a), the pitch P1 of the holes in the article longitudinal direction X is smaller than the pitch P2 of the elastic members 24 in the article longitudinal direction X. As shown in FIG. 8(a), the pitch P2 of the elastic members 24 in the article longitudinal direction X is the distance between the centers of elastic members 24 that are adjacent to each other in article longitudinal direction X.

From a similar standpoint to that described above, the pitch P1 of the holes in the article longitudinal direction X is preferably 20% or greater, and more preferably 30% or greater, is preferably 90% or less, and more preferably 80% or less, and is preferably from 20% to 90% and more preferably from 30% to 80%, with respect to the pitch P2 of the elastic members 24 in the article longitudinal direction X.

Moreover, the pitch P2 of the elastic members 24 in the article longitudinal direction X is preferably 3 mm or greater, and more preferably 4 mm or greater, is preferably 12 mm or less, and more preferably 10 mm or less, and is preferably from 3 to 12 mm and more preferably from 4 to 10 mm.

It should be noted that the pitch P2 of the elastic members 24 in the article longitudinal direction X is measured in a state (uncontracted state) in which the elasticized portion G is stretched in the article lateral direction.

Moreover, from the standpoint of even more reliably achieving the above-described bellows effect, it is preferable that as shown in FIG. 8(a), the pitch P4 of the holes in the article lateral direction Y is equal to or smaller than the pitch P5 of the folds in the article lateral direction Y. The pitch P5 of the folds in the article lateral direction Y is the distance between the center lines 36c passing through the centers of non-joined regions 36 that are adjacent to each other in the article lateral direction Y. The above-described center lines 36c substantially coincide with the centers of ridge portions 29a of the respective folds 29. The center of each ridge portion 29a is the middle point between groove portions 29b that are adjacent to each other in the article lateral direction Y.

From a similar standpoint to that described above, the pitch P4 of the holes in the article lateral direction Y is preferably 20% or greater, and more preferably 30% or greater, is preferably 90% or less, and more preferably 80% or less, and is preferably from 20% to 90% and more preferably from 30% to 80%, with respect to the pitch P5 of the folds in the article lateral direction Y. From a similar standpoint to that described above, the pitch P5 of the folds in the article lateral direction Y is preferably 3 mm or greater, and more preferably 5 mm or greater, is preferably 18 mm or less, and more preferably 15 mm or less, and is preferably from 3 to 18 mm and more preferably from 5 to 15 mm.

It should be noted that the pitch P4 of the holes in the article lateral direction Y and the pitch P5 of the folds in the article lateral direction Y are measured in a state (uncontracted state) in which the elasticized portion G is stretched in the article lateral direction.

Although the outline of the holes m that overlap the elastic members 24 according to the present embodiment has a circular shape as shown in FIG. 3, the outline of those holes may also have other shapes, such as an elliptical shape, a square shape, and an oblong shape, in addition to a circular shape. In light of the tactile feel, it is preferable that the shape of the skin-facing surface-side opening m2 of each hole m has a curve portion. Examples of the outline that has a curve portion include shapes such as the circular shape shown in FIG. 3, an oval shape, and an elliptical shape.

It is preferable that the non-skin-facing surface-side opening m1 and the skin-facing surface-side opening m2 of each hole m individually have a shape with a curve portion in a plan view. Moreover, it is preferable that the holes m' that do not overlap the elastic members 24 also have a similar outline to the holes m that overlap the elastic members 24.

The above-described diaper 1 will be further described. The side seals 4 described above are formed after formation of the joined portions 26, by placing each outer lateral side fixing region 27 on the front portion A side and the corresponding one of the outer lateral side fixing regions 27 on the rear portion B side one on top of the other and subjecting the resulting overlapping portions to hot embossing. For the processing for forming the joined portions 26, ultrasonic sealing, a laser, and the like can also be employed instead of hot embossing. For the processing for forming the side seals 4, ultrasonic sealing, a laser, an adhesive, and the like can also be employed instead of hot embossing.

The absorbent assembly 3 has a liquid permeable topsheet 31, a semi-liquid permeable backsheet 32, and an absorbent member 33 disposed between the topsheet 31 and the backsheet 32. The semi-liquid permeability includes liquid impermeability and semi-liquid permeability. Moreover, a pair of leak-proof cuff forming sheets 34,34 are arranged on both lateral side portions of the absorbent assembly 3. Each of the leak-proof cuff forming sheets 34 has an elastic member 35 for forming leak-proof cuffs, in the vicinity of an end edge of that leak-proof cuff forming sheet 34 that is located close to the article longitudinal direction center line CL. When the diaper is worn, the contracting force of the elastic member 35 causes a portion of the leak-proof cuff forming sheet 34 that has a predetermined width from the aforementioned end edge to stand upright so as to move away from the topsheet 31 and thus form the leak-proof cuffs.

Materials for forming the various portions of the diaper 1 will be described. For each of the topsheet 31, the backsheet 32, the absorbent member 33, the leak-proof cuff forming sheets 34, and the like, materials similar to those conventionally used in absorbent articles of this type can be used without limitation. For example, a liquid permeable nonwoven fabric, a perforated film, a laminate of these, and the like can be used as the topsheet 31, and a resin film, a laminate of a resin film and a nonwoven fabric, and the like can be used as the backsheet 32. An absorbent member, for example, obtained by wrapping an absorbent core composed of a fiber aggregate of a fiber material such as pulp, or an absorbent core in which a superabsorbent polymer is supported on the aforementioned absorbent core, in a core-wrap sheet composed of tissue paper, a water permeable nonwoven fabric, or the like can be used as the absorbent member 33. An elastic film, a water repellent nonwoven fabric, a woven fabric, a laminated sheet of these, or the like can be used as the leak-proof cuff forming sheets 34.

Various types of sheet materials conventionally used in articles of this type can be used, without limitation, as the sheet material composing the outer sheet 22 and the inner sheet 23. However, a nonwoven fabric is preferable, and in particular, in light of flexibility and the like, a single-layer nonwoven fabric composed of an air-through nonwoven fabric, a heat-rolled nonwoven fabric, a spunlaced nonwoven fabric, a spunbonded nonwoven fabric, a melt-blown nonwoven fabric, or the like or a laminated nonwoven fabric constituted by two or more layers is preferable. Moreover, a sheet into which any of these nonwoven fabrics and a film are integrated may also be used. It should be noted that an exterior sheet composed of a nonwoven fabric, a film, or the like can also be disposed on a non-skin-facing surface side of the backsheet 32 in the crotch portion C.

Various types of known elastic materials used in absorbent articles such as disposable diapers and sanitary napkins can be used, without limitation, as the material for forming the elastic members 24 and 35. Examples of the raw material for forming the elastic materials include synthetic rubber, such as styrene-butadiene, butadiene, isoprene, and neoprene, natural rubber, EVA, elastic polyolefin, and polyurethane. With respect to the form of the elastic members, filamentous elastic members (rubber thread or the like) or string-like elastic members (flat rubber string or the like) having a rectangular, square, circular, or polygonal cross-sectional shape, for example, or multifilament-type filamentous elastic members or the like can be preferably used.

In the foregoing description, the present invention has been described based on the preferred embodiments. However, the present invention is not limited to the foregoing embodiments, and appropriate changes can be made thereto.

For example, an outer cover that is not divided into the front panel 2A and the rear panel 2B may be adopted as the outer cover. For example, a configuration may be adopted in which the outer sheet 22 and the inner sheet 23 of the outer cover are each composed of a single sheet that is continuous over the front portion A, the crotch portion C, and the rear portion B, or a configuration may be adopted in which, while the outer sheet 22 of the outer cover is composed of a single sheet that is continuous over the front portion A, the crotch portion C, and the rear portion B, the inner sheet 23 of the outer cover is disposed in only one of the front portion A and the rear portion B.

Moreover, the below-waist lower elasticized portions G2 may develop elasticity continuously from one of the lateral side regions S to the other lateral side region S. Moreover, the absorbent article of the present invention may have only either the waist elasticized portions G1 or the below-waist lower elasticized portions G2. Moreover, the absorbent article of the present invention may have one or both of the waist elasticized portion G1 and the below-waist lower elasticized portions G2 in only either the front portion A or the rear portion B, instead of having the waist elasticized portion G1 and the below-waist lower elasticized portions G2 in both of the front portion A and the rear portion B.

Moreover, the absorbent article of the present invention may have the holes m that overlap the elastic members 24 in only one of the front portion A and the rear portion B. In light of breathability, it is preferable that the holes m are formed in at least the rear portion B.

Moreover, a configuration may be adopted in which the holes m that overlap the elastic members 24 and holes that do not overlap the elastic members 24 are formed in a regularly or irregularly arranged manner in both or one of the front portion A and the rear portion B.

Moreover, in the case where the absorbent article has both the holes m that overlap the elastic members 24 and the holes m' that do not overlap the elastic members 24, it is preferable that the holes m' that do not overlap the elastic members 24 have a similar configuration to that of the holes m that overlap the elastic members 24.

Moreover, a configuration may also be adopted in which the absorbent article of the present invention has only the holes m that overlap the elastic members 24 as the holes formed in the outer sheet 22.

Moreover, although the outer cover 2 in the front portion A or the rear portion B may have a configuration in which only the sheet material composing the outer sheet is folded back along the circumferential edge portion of the waist opening as in the case of the diaper 1 described above, a configuration may also be adopted in which the sheet material composing the outer sheet and the sheet material composing the inner sheet are folded back together, or a configuration may also be adopted in which none of the outer sheet and the inner sheet have a folded-back portion. Moreover, the folded-back portion of the outer sheet or the inner sheet may be joined to the opposing surface in a manner different from that of the diaper 1 described above. For example, a configuration in which the entire region of the folded-back portion is joined to the opposing surface, or other configurations can also be adopted.

Moreover, the absorbent article of the present invention is not limited to a pull-on absorbent article, and may also be a so-called open type disposable diaper. Examples of the pull-on absorbent article include pull-on sanitary napkins and the like in addition to infant or adult pull-on disposable diapers. The open type disposable diaper is typically provided with a piece of fastening tape on both lateral side portions of the rear portion, the pieces of fastening tape each having a pressure-sensitive adhesive portion or an attachment portion composed of a hook member or the like of a mechanical hook-and-loop fastener, and the open type disposable diaper is worn by attaching the pieces of fastening tape to a piece of landing tape provided on the outer surface of the front portion.

Moreover, the hole making processing may be performed before or after the joined region forming step. From the stand point of accurately forming the holes m at predetermined specific locations relative to the elastic members 24, and from the standpoint of preventing the elastic members 24 from being cut due to the hole making processing, it is preferable that the hole making processing is performed before the joined region forming step.

Moreover, in the diaper 1 of the present embodiment, the joined regions 26 that are formed intermittently extending in the article longitudinal direction X and the non-joined regions 36 extending in the article longitudinal direction X are alternatingly arranged side-by-side in the article lateral direction Y, and the joined regions 26 that are formed intermittently extending in the article lateral direction Y and the non-joined regions 36 extending in the article lateral direction Y are alternatingly arranged side-by-side in the article longitudinal direction X; however, the joined regions 26 may also continuously extend in the article longitudinal direction X.

With regard to the above-described embodiments of the present invention, the present invention further discloses the following absorbent articles.

<1> An absorbent article having a front portion to be disposed on a front side of a wearer, a rear portion to be disposed on a rear side of the wearer, and a crotch portion located between the front portion and the rear portion, the absorbent article comprising an elasticized portion that is stretchable and contractible in an article lateral direction in at least one of the front portion and the rear portion, wherein the elasticized portion has an outer sheet to be disposed on a side that is away from the skin of the wearer, an inner sheet to be disposed on a side that is closer to the skin of the wearer than the outer sheet is, and a plurality of elastic members that are arranged between the outer and inner sheets in a state in which the elastic members are stretched in the article lateral direction, the outer sheet and the inner sheet are partially joined to each other at a joined region, the joined region is sandwiched between non-joined regions where the outer sheet and the inner sheet are not continuously joined to each other in an article longitudinal direction or the article lateral direction, a plurality of the joined regions and a plurality of the non-joined regions are repeatedly arranged in the article longitudinal direction or the article lateral direction, the outer sheet is configured to be deformable so as to bulge toward a non-skin-facing surface side due to contraction of the elastic members and form a plurality of folds along the article longitudinal direction, and the absorbent article has holes penetrating the outer sheet at positions in the folds formed by the outer sheet, the positions overlapping the elastic members in a thickness direction.

<2> The Absorbent Article as Set Forth in Clause <1>, wherein a non-skin-facing surface-side opening of each hole is larger than a skin-facing surface-side opening thereof.

<3> the Absorbent Article as Set Forth in Clause <1> or <2>, wherein the outer sheet comprises, inward of an outer circumferential edge of each hole, a portion in which the thickness of the outer sheet gradually decreases toward a center portion of the hole.

<4> The Absorbent Article as Set Forth in any One of Clauses <1> to <3>, wherein each hole comprises a depressed portion in which the cross-sectional area of the hole in a direction that is perpendicular to the thickness direction of the outer sheet gradually decreases toward a skin-facing surface side in the thickness direction, and a communication portion which is located closer to the skin-facing surface side than the depressed portion is and in which the cross-sectional area is constant, and the thickness of the communication portion in the thickness direction of the outer sheet is 80% or less of the total thickness of the depressed portion and the communication portion.

<5> The Absorbent Article as Set Forth in Clause <4>,
wherein the thickness T4 of the communication portion in the thickness direction Z of the outer sheet is preferably 5% or greater, and more preferably 10% or greater and is preferably 80% or less, and more preferably 70% or less, with respect to the total thickness T of the depressed portion and the communication portion.

<6> The Absorbent Article as Set Forth in any One of Clauses <1> to <5>,
wherein a circumferential edge portion of a skin-facing surface-side opening of each hole protrudes farther toward a skin-facing surface side than a position of a skin-facing surface of a section of the outer sheet other than the holes.

<7> The Absorbent Article as Set Forth in Clause <6>,
wherein, in each hole, the thickness of a portion of the circumferential edge portion that protrudes from the skin-facing surface of the outer sheet is smaller than the thickness of the section of the outer sheet other than the holes.

<8> The Absorbent Article as Set Forth in Clause <6> or <7>,
wherein, in each hole, the thickness T20 of the portion of the circumferential edge portion that protrudes from the skin-facing surface of the outer sheet is preferably 5% or greater, and more preferably 10% or greater and is preferably 80% or less, and more preferably 70% or less, with respect to the thickness T22 of the section of the outer sheet other than the holes.

<9> The Absorbent Article as Set Forth in any One of Clauses <1> to <8>,
wherein the inter-fiber distance of the outer sheet in a portion of each hole that is located inward of an outer circumferential edge of the hole is smaller than the inter-fiber distance of a section of the outer sheet other than the holes.

<10> The Absorbent Article as Set Forth in any One of Clauses <1> to <9>,
wherein the absorbent article includes an outer cover that has the elasticized portion and an absorbent assembly that is fixed to the outer cover, and, in a region between a rear end portion of the absorbent article and a rear end portion of the absorbent assembly in the article longitudinal direction or a region between a front end portion of the absorbent article and a front end portion of the absorbent assembly in the article longitudinal direction, the number of the holes that overlap the elastic members is preferably 5% or greater, and more preferably 8% or greater and is preferably 80% or less, and more preferably 70% or less, with respect to the total number of holes in the region.

<11> the Absorbent Article as Set Forth in any One of Clauses <2> to <10>,
wherein the opening diameter of the non-skin-facing surface-side opening of each hole is preferably 110% or greater, and more preferably 120% or greater and is preferably 300% or less, and more preferably 200% or less, with respect to the opening diameter of the skin-facing surface-side opening thereof.

<12> the Absorbent Article as Set Forth in any One of Clauses <2> to <11>,
wherein the area of the skin-facing surface-side opening of each hole is preferably 120% or greater, and more preferably 130% or greater and is preferably 500% or less, and more preferably 400% or less, with respect to the area of the non-skin-facing surface-side opening thereof.

<13> the Absorbent Article as Set Forth in any One of Clauses <1> to <12>,
wherein the opening diameter of a skin-facing surface-side opening of each hole is from 0.5 to 3 mm.

<14> the Absorbent Article as Set Forth in any One of Clauses <1> to <13>,
wherein the area of a skin-facing surface-side opening of each hole is preferably 0.1 mm$^2$ or greater, and more preferably 0.2 mm$^2$ or greater and is preferably 9 mm$^2$ or less, and more preferably 7 mm$^2$ or less.

<15> the Absorbent Article as Set Forth in any One of Claims <1> to <14>,
wherein a plurality of the holes are intermittently formed in the article longitudinal direction in the folds formed by the outer sheet, and
the pitch of the holes in the article longitudinal direction is equal to or smaller than the pitch of the elastic members in the article longitudinal direction.

<16> the Absorbent Article as Set Forth in any One of Clauses <1> to <15>,
wherein the pitch P1 of the holes in the article longitudinal direction is smaller than the pitch P2 of the elastic members in the article longitudinal direction.

<17> the Absorbent Article as Set Forth in Clause <16>,
wherein the pitch P1 of the holes in the article longitudinal direction is preferably 20% or greater, and more preferably 30% or greater and is preferably 90% or less, and more preferably 80% or less, with respect to the pitch P2 of the elastic members in the article longitudinal direction.

<18> the Absorbent Article as Set Forth in any One of Clauses <1> to <17>,
wherein a plurality of the holes are intermittently formed in the article longitudinal direction in the folds formed by the outer sheet, and
the pitch of the holes in the article longitudinal direction is from 1 to 10 mm.

<19> the Absorbent Article as Set Forth in any One of Clauses <1> to <18>,
wherein a plurality of the holes are intermittently formed in the article lateral direction in the folds formed by the outer sheet, and
the pitch of the holes in the article lateral direction is from 1 to 10 mm.

<20> the Absorbent Article as Set Forth in any One of Clauses <1> to <19>,
wherein the joined regions are formed intermittently or continuously extending in the article longitudinal direction, and, in the article lateral direction, the joined regions are sandwiched between the non-joined regions where the outer sheet and the inner sheet are not continuously joined to each other in the article longitudinal direction, and
the folds along the article longitudinal direction are configured to be formed in the non-joined regions of the outer sheet between the joined regions adjacent to one another in the article lateral direction.

<21> The Absorbent Article as Set Forth in Clause <20>,
wherein the pitch of the joined regions in the article lateral direction is from 4 to 10 mm.
<22> The Absorbent Article as Set Forth in Clause <20> or <21>,
wherein the joined regions constitute joined region rows that are formed intermittently extending in the article longitudinal direction and are formed at intervals in the article lateral direction.
<23> The Absorbent Article as Set Forth in any One of Clauses <1> to <22>,
wherein a plurality of the holes are intermittently formed in the article lateral direction in the folds formed by the outer sheet, and
the pitch of the holes in the article lateral direction is equal to or smaller than the pitch of the folds in the article lateral direction.
<24> The Absorbent Article as Set Forth in any One of Clauses <20> to <23>,
wherein the pitch P4 of the holes in the article lateral direction is preferably 20% or greater, and more preferably 30% or greater and is preferably 90% or less, and more preferably 80% or less, with respect to the pitch P5 of the folds in the article lateral direction.
<25> The Absorbent Article as Set Forth in any One of Clauses <20> to <24>,
wherein the pitch P5 of the folds in the article lateral direction is preferably 3 mm or greater, and more preferably 5 mm or greater and is preferably 18 mm or less.
<26> The Absorbent Article as Set Forth in any One of Clauses <20> to <25>,
wherein the joined regions intermittently extend in the article longitudinal direction, and are sandwiched between the non-joined regions where the outer sheet and the inner sheet are not continuously joined to each other in the article lateral direction, and
the folds along the article longitudinal direction are configured to be formed in the non-joined regions of the outer sheet between the joined regions adjacent to one another in the article lateral direction.
<27> The Absorbent Article as Set Forth in any One of Clauses <20> to <26>,
wherein the elastic members are arranged between the joined regions adjacent to one another in the article longitudinal direction.
<28> The Absorbent Article as Set Forth in any One of Clauses <20> to <27>,
wherein the pitch P1 of the holes in the article longitudinal direction is preferably 20% or greater, and more preferably 30% or greater and is preferably 90% or less, and more preferably 80% or less, with respect to the pitch P3 of the joined regions 26a in the article longitudinal direction.
<29> The Absorbent Article as Set Forth in any One of Clauses <15> to <27>,
wherein the pitch P1 of the holes in the article longitudinal direction is preferably 1 mm or greater, and more preferably 2 mm or greater and is preferably 10 mm or less, and more preferably 8 mm or less.
<30> The Absorbent Article as Set Forth in any One of Clauses <20> to <29>,
wherein the pitch P3 of the joined regions in the article longitudinal direction is preferably 4 mm or greater, and more preferably 5 mm or greater and is preferably 10 mm or less, and more preferably 8 mm or less.

<31> The Absorbent Article as Set Forth in any One of Clauses <1> to <30>,
wherein the pitch of the elastic members in the article longitudinal direction is preferably 3 mm or greater, and more preferably 4 mm or greater and is preferably 12 mm or less, and more preferably 10 mm or less.
<32> The Absorbent Article as Set Forth in any One of Clauses <1> to <31>,
wherein the pitch of the elastic members in the article longitudinal direction is from 3 to 12 mm.
<33> The Absorbent Article as Set Forth in any One of Clauses <1> to <32>,
wherein an outline of each hole has a shape composed of a curve.
<34> The Absorbent Article as Set Forth in any One of Clauses <1> to <33>,
wherein a non-skin-facing surface-side opening and a skin-facing surface-side opening of each hole individually have a shape with a curve portion in a plan view.
<35> The Absorbent Article as Set Forth in any One of Clauses <1> to <34>,
wherein the holes are formed so that an outline of each hole in a cross section taken along the thickness direction is curved.
<36> The Absorbent Article as Set Forth in any One of Clauses <1> to <35>,
wherein the holes are formed in sections of the folds other than the joined regions.
<37> The Absorbent Article as Set Forth in any One of Clauses <1> to <36>,
wherein the holes overlap center lines that pass through the centers of the respective non-joined regions in the article lateral direction.
<38> The Absorbent Article as Set Forth in any One of Clauses <1> to <37>,
wherein, in the folds, top portions of protruding portions of the individual folds are circular-arc-shaped in cross section.
<39> The Absorbent Article as Set Forth in any One of Clauses <1> to <38>,
wherein the absorbent article is a pull-on absorbent article including an outer cover that has the elasticized portion and an absorbent assembly that is fixed to the outer cover, and both lateral side portions of the front portion are respectively joined to both lateral side portions of the rear portion to thereby form a pair of side seals and a waist opening.
<40> the Absorbent Article as Set Forth in Clause <39>,
wherein the absorbent article has a waist elasticized portion in a circumferential edge portion of the waist opening, as the elasticized portion to be disposed on a waist portion of the wearer when the absorbent article is worn, and
the total area of the holes in the waist elasticized portion is preferably 2% or greater, and more preferably 4% or greater and is preferably 30% or less, and more preferably 25% or less, with respect to the area of the waist elasticized portion.
<41> the Absorbent Article as Set Forth in Clause <40>,
wherein the absorbent article has a below-waist lower elasticized portion as the elasticized portion that is formed at a location below the waist elasticized portion and above lower ends of the side seals, and
the total area of the holes in the below-waist lower elasticized portion is preferably 2% or greater, and more preferably 4% or greater and is preferably 30% or less, and more preferably 25% or less, with respect to the area of the below-waist lower elasticized portion.

<42> the Absorbent Article as Set Forth in Clause <40> or <41>,
wherein the absorbent article has a pair of outer lateral side fixing regions where the outer sheet and the inner sheet are joined to each other via an adhesive, the outer lateral side fixing regions being respectively located on opposite sides of a longitudinal direction center line that bisects the absorbent article in the article lateral direction,
a plurality of the elastic members are arranged spanning between the pair of outer lateral side fixing regions in the waist elasticized portion, and
the plurality of elastic members are fixed between the outer sheet and the inner sheet in each of the pair of outer lateral side fixing regions, but are not fixed to any of the outer sheet and the inner sheet between the pair of outer lateral side fixing regions.

<43> the Absorbent Article as Set Forth in any One of Clauses <39> to <42>,
wherein the absorbent article has an assembly-side fixing region where the outer sheet and the inner sheet are joined to each other via an adhesive, in the vicinity of the position of a lateral side edge of the absorbent assembly, the lateral side edge extending along the article longitudinal direction, and
the assembly-side fixing region is formed so as to entirely overlap the absorbent assembly.

INDUSTRIAL APPLICABILITY

According to the present invention, an absorbent article that has excellent breathability is provided.

The invention claimed is:

1. An absorbent article having a front portion to be disposed on a front side of a wearer, a rear portion to be disposed on a rear side of the wearer, and a crotch portion located between the front portion and the rear portion, the absorbent article comprising an elasticized portion that is stretchable and contractible in an article lateral direction in at least one of the front portion and the rear portion,
wherein the elasticized portion has an outer sheet to be disposed on a side that is away from the skin of the wearer, an inner sheet to be disposed on a side that is closer to the skin of the wearer than the outer sheet is, and a plurality of elastic members that are arranged between the outer and inner sheets in a state in which the elastic members are stretched in the article lateral direction,
the outer sheet and the inner sheet are partially joined to each other at a joined region,
the joined region is sandwiched between non-joined regions where the outer sheet and the inner sheet are not continuously joined to each other in an article longitudinal direction or the article lateral direction,
a plurality of the joined regions and a plurality of the non-joined regions are repeatedly arranged in the article longitudinal direction or the article lateral direction, the outer sheet is configured to be deformable so as to bulge toward a non-skin-facing surface side due to contraction of the elastic members and form a plurality of folds along the article longitudinal direction, and
the absorbent article has holes penetrating the outer sheet at positions in the folds formed by the outer sheet, the positions overlapping the elastic members in a thickness direction,
wherein the holes are formed in the non joined regions and not in the joined regions.

2. The absorbent article according to claim 1,
wherein a non-skin-facing surface-side opening of each hole is larger than a skin-facing surface-side opening thereof.

3. The absorbent article according to claim 1,
wherein the outer sheet comprises, inward of an outer circumferential edge of each hole, a portion in which a thickness of the outer sheet gradually decreases toward a center portion of the hole.

4. The absorbent article according to claim 1,
wherein each hole comprises a depressed portion in which a cross-sectional area of the hole in a direction that is perpendicular to the thickness direction of the outer sheet gradually decreases toward a skin-facing surface side in the thickness direction, and a communication portion which is located closer to the skin-facing surface side than the depressed portion is and in which the cross-sectional area is constant, and
a thickness of the communication portion in the thickness direction of the outer sheet is 80% or less of a total thickness of the depressed portion and the communication portion.

5. The absorbent article according to claim 1,
wherein a circumferential edge portion of a skin-facing surface-side opening of each hole protrudes farther toward a skin-facing surface side than a position of a skin-facing surface of a section of the outer sheet other than the holes.

6. The absorbent article according to claim 5,
wherein, in each hole, a thickness of a portion of the circumferential edge portion that protrudes from the skin-facing surface of the outer sheet is smaller than a thickness of the section of the outer sheet other than the holes.

7. The absorbent article according to claim 1,
wherein an inter-fiber distance of the outer sheet in a portion of each hole that is located inward of an outer circumferential edge of the hole is smaller than an inter-fiber distance of a section of the outer sheet other than the holes.

8. The absorbent article according to claim 1,
wherein the absorbent article includes an outer cover that has the elasticized portion and an absorbent assembly that is fixed to the outer cover, and, in a region between a rear end portion of the absorbent article and a rear end portion of the absorbent assembly in the article longitudinal direction or a region between a front end portion of the absorbent article and a front end portion of the absorbent assembly in the article longitudinal direction, a number of the holes that overlap the elastic members is 5% or greater with respect to a total number of holes in the region.

9. The absorbent article according to claim 1,
wherein an opening diameter of a non-skin-facing surface-side opening of each hole is 110% or greater with respect to an opening diameter of a skin-facing surface-side opening thereof.

10. The absorbent article according to claim 1,
wherein an opening diameter of a skin-facing surface-side opening of each hole is from 0.5 to 3 mm.

11. The absorbent article according to claim 1,
wherein a plurality of the holes are intermittently formed in the article longitudinal direction in the folds formed by the outer sheet, and a pitch of the holes in the article longitudinal direction is equal to or smaller than a pitch of the elastic members in the article longitudinal direction.

12. The absorbent article according to claim 1,
wherein a plurality of the holes are intermittently formed in the article longitudinal direction in the folds formed by the outer sheet, and
a pitch of the holes in the article longitudinal direction is from 1 to 10 mm.

13. The absorbent article according to claim 1,
wherein a plurality of the holes are intermittently formed in the article lateral direction in the folds formed by the outer sheet, and
a pitch of the holes in the article lateral direction is from 1 to 10 mm.

14. The absorbent article according to claim 1,
wherein the joined regions are formed intermittently or continuously extending in the article longitudinal direction, and, in the article lateral direction, the joined regions are sandwiched between the non-joined regions where the outer sheet and the inner sheet are not continuously joined to each other in the article longitudinal direction, and
the folds along the article longitudinal direction are configured to be formed in the non-joined regions of the outer sheet between the joined regions adjacent to one another in the article lateral direction.

15. The absorbent article according to claim 14,
wherein the joined regions constitute joined region rows that are formed intermittently extending in the article longitudinal direction and are formed at intervals in the article lateral direction.

16. The absorbent article according to claim 14,
wherein a plurality of the holes are intermittently formed in the article lateral direction in the folds formed by the outer sheet, and
a pitch of the holes in the article lateral direction is equal to or smaller than a pitch of the folds in the article lateral direction.

17. The absorbent article according to claim 1,
wherein the joined regions intermittently extend in the article longitudinal direction, and are sandwiched between the non-joined regions where the outer sheet and the inner sheet are not continuously joined to each other in the article lateral direction, and
the folds along the article longitudinal direction are configured to be formed in the non-joined regions of the outer sheet between the joined regions adjacent to one another in the article lateral direction.

18. The absorbent article according to claim 1,
wherein the elastic members are arranged between the joined regions adjacent to one another in the article longitudinal direction.

19. The absorbent article according to claim 1,
wherein a pitch of the elastic members in the article longitudinal direction is from 3 to 12 mm.

20. The absorbent article according to claim 1,
wherein an outline of each hole has a shape composed of a curve.

* * * * *